(12) United States Patent  
Gao et al.

(10) Patent No.: US 9,790,213 B2
(45) Date of Patent: Oct. 17, 2017

(54) IMIDAZOLES FOR THE TREATMENT AND PROPHYLAXIS OF RESPIRATORY SYNCYTIAL VIRUS INFECTION

(71) Applicant: Hoffmann-La Roche Inc., Little Falls, NJ (US)

(72) Inventors: Lu Gao, Shanghai (CN); Chungen Liang, Shanghai (CN); Lisha Wang, Basel (CH); Hongying Yun, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/216,165

(22) Filed: Jul. 21, 2016

(65) Prior Publication Data

US 2016/0326148 A1 Nov. 10, 2016

Related U.S. Application Data

(63) Continuation of application No. PCT/EP2015/050829, filed on Jan. 19, 2015.

(51) Int. Cl.
*C07D 413/04* (2006.01)
(52) U.S. Cl.
CPC .................. *C07D 413/04* (2013.01)
(58) Field of Classification Search
CPC .................................................. C07D 413/04
See application file for complete search history.

(56) References Cited

FOREIGN PATENT DOCUMENTS

| EP | 2427447 A2 | 3/2014 | |
|---|---|---|---|
| WO | WO 2010127152 A2 * | 11/2010 | ........... C07D 401/04 |
| WO | WO 2015110369 A1 * | 7/2015 | ........... C07D 413/04 |

OTHER PUBLICATIONS

International Preliminary Report on Patentability issued on International Application No. PCT/EP2015/050829, issued Jul. 26, 2016, in 6 pages.
International Search Report issued on International Application No. PCT/EP2015/050829, mailed Mar. 11, 2015, in 4 pages.
Krilov, "Recent developments in the treatment and prevention of respiratory syncytial virus infection" Expert Opin. Ther. Patents 12(3):441-449 (2002).
Written Opinion of the International Searching Authority issued in International Application No. PCT/EP2015/050829, dated Mar. 11, 2015, in 5 pages.

* cited by examiner

*Primary Examiner* — Matthew Coughlin
(74) *Attorney, Agent, or Firm* — Kevin M. Clark

(57) ABSTRACT

The invention provides novel compounds having the general formula:

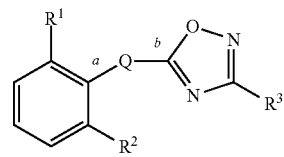

wherein $R^1$, $R^2$, $R^3$ and Q are as described herein, compositions including the compounds and methods of using the compounds.

8 Claims, No Drawings

IMIDAZOLES FOR THE TREATMENT AND PROPHYLAXIS OF RESPIRATORY SYNCYTIAL VIRUS INFECTION

RELATED APPLICATIONS

This application is a continuation of International Application No. PCT/EP2015/050829, having an international filing date of Jan. 19, 2015, and which claims benefit under 35 U.S.C §119 to PCT/CN2014/070973 having an international filing date of Jan. 21, 2014 and of PCT/CN2014/077042 having an international filing date of May 8, 2014. The entire contents of International Application No. PCT/EP2015/050829 are hereby incorporated herein by reference.

The present invention relates to organic compounds useful for therapy and/or prophylaxis in a mammal, and in particular to respiratory syncytial virus (RSV) inhibitors useful for treating RSV infection.

FIELD OF THE INVENTION

Human respiratory syncytial virus (RSV) is an enveloped, medium-sized (120 to 300 nm) RNA virus with a nonsegmented, single-stranded, negative-sense genome that is associated with viral proteins throughout its length, which forms the nucleocapsid. The viral RNA consists of 15,222 nucleotides that are transcribed into 10 monocistronic polyadenylated messenger RNAs (mRNAs), each of which encodes for one of the major proteins, except for M2 mRNA, that possesses two overlapping open reading frames that encode for two separate proteins (M2-1, the transcription processivity factor, and M2-2, a regulatory protein).

Respiratory syncytial virus is distributed worldwide and appears in yearly epidemics. Respiratory syncytial virus outbreaks often overlap with outbreaks of influenza and human metapneumovirus but are generally more consistent from year to year and result in more disease overall, especially among infants<6 months of age.

Children with RSV infection are very contagious, resulting in high attack rates. Infection is almost universal by the $2^{nd}$ birthday. Reinfection occurs at a rate of 10-20% per epidemic throughout childhood, with a lower frequency among adults. Primary infections with RSV frequently involve the lower respiratory tract, particularly among infants within the first several months of life. Most commonly these present as bronchiolitis, followed by pneumonia and tracheobronchitis. Upper respiratory tract signs almost always accompany the lower respiratory tract disease, or the infection may be confined to the upper respiratory tract, which in young children is commonly associated with fever and otitis media.

Respiratory syncytial virus is the most frequent cause of bronchiolitis and is estimated to cause 40% to 90% of bronchiolitis hospitalizations and up to 50% of pneumonia admissions among infants.

The development of RSV vaccines has not been successful, possibly due to immunologic immaturity of the infants and the immunosuppressive effects of maternal antibodies. Currently, aerosolized ribavirin (Valeant) is the only approved treatment for RSV disease. Its clinical efficacy has been controversial. In addition, palivizumab (Synagis®, MedImmune) is approved for prophylactic use in selected high-risk infants and was demonstrated 45-55% reduction in hospitalization rate in two separate Phase III clinical trials. However, its high cost limited its usage in a small group of infants within developed countries. A number of small molecule RSV inhibitors have been discovered. Among them, only a few reached Phase I or II clinical trials. Arrow Therapeutics (now a group in AstraZeneca, UK) completed a five-year Phase II trial of nucleocapsid (N) protein inhibitor RSV-604 in stem cell transplantation patients by February 2010 (www.clinicaltrials.gov), but has not released the final results. Most of other small molecules were put on hold for various reasons. RNAi therapeutics against RSV has also been thoroughly studied. ALN-RSV01 (Alnylam Pharmaceuticals, MA, USA) is a siRNA targeting on RSV gene. A nasal spay administered for two days before and for three days after RSV inoculation decreased infection rate among adult volunteers (DeVincenzo J. et al, Proc Natl Acad Sci USA. 2010 May 11; 107(19): 8800-5). In Phase II trial using naturally infected lung transplantation patients, results were not sufficient for conclusion of antiviral efficacy, though certain health benefits have been observed (Zamora M R et al, Am J Respir Crit Care Med. 2011 Feb. 15; 183(4): 531-8).

Therefore, there is an urgent and unmet medical need for developing novel therapies to treat RSV infections.

SUMMARY OF THE INVENTION

Objects of the present invention are novel compounds of formula I, their manufacture, medicaments based on a compound in accordance with the invention and their production as well as the use of compounds of formula I for the treatment or prophylaxis of RSV infection.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$ alkyl" groups are methyl, ethyl, isopropyl and tert-butyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy and the like. Particular "$C_{1-6}$alkoxy" groups are methoxy and ethoxy and more particularly methoxy.

The term "halogen" means fluorine, chlorine, bromine or iodine. Particular halogen is fluorine, chlorine or bromine.

The term "hydroxy" alone or in combination refers to the group —OH.

The term "carboxy" alone or in combination refers to the group —COOH.

The term "carbonyl" alone or in combination refers to the group —C(O)—.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitors of RSV

The present invention provides (i) novel compounds having the general formula I:

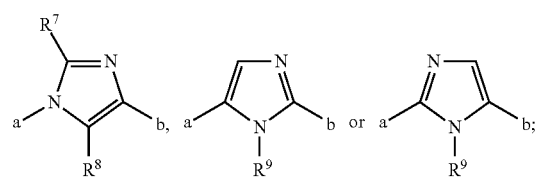

wherein
$R^1$ is hydrogen, $C_{1-6}$alkyl, $C_{1-6}$alkoxy or halogen;
$R^2$ is hydrogen, $C_{1-6}$alkyl or halogen;
provided that $R^1$ and $R^2$ are not hydrogen simultaneously;
$R^3$ is

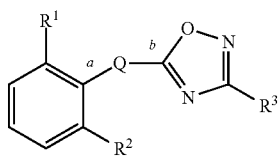

wherein $R^4$ is $C_{1-6}$alkoxy, $C_{1-6}$alkoxycarbonyl, carboxy or halogen;
$R^5$ is hydrogen, $C_{1-6}$alkyl or $C_{1-6}$alkoxy;
$R^6$ is hydrogen or $C_{1-6}$alkoxy;
Q is

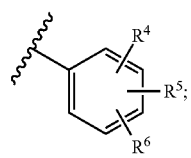

wherein $R^7$ is hydrogen, $C_{1-6}$alkyl, carboxy, hydroxy-$CH_2$— or halogen;
$R^8$ is hydrogen or $C_{1-6}$alkyl;
$R^9$ is $C_{1-6}$alkyl;
or pharmaceutically acceptable salts thereof.

Further embodiment of present invention is (ii) a compound of formula I, wherein
$R^1$ is hydrogen, methyl, methoxy, chloro or bromo;
$R^2$ is hydrogen, methyl or chloro;
provided that $R^1$ and $R^2$ are not hydrogen simultaneously;
$R^3$ is

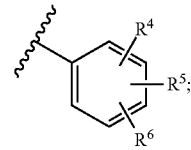

wherein $R^4$ is methoxy, methoxycarbonyl, carboxy or fluoro;
$R^5$ is hydrogen, methyl or methoxy;
$R^6$ is hydrogen or methoxy;
Q is

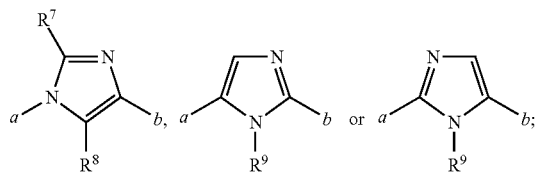

wherein $R^7$ is hydrogen, methyl, carboxy, hydroxy-$CH_2$— or bromo;
$R^8$ is hydrogen or methyl;
$R^9$ is methyl;
or pharmaceutically acceptable salts thereof.

Another embodiment of present invention is (iii) a compound of formula I or a pharmaceutically acceptable salt thereof, wherein
$R^1$ is $C_{1-6}$alkyl or halogen;
$R^2$ is hydrogen or $C_{1-6}$alkyl;
$R^3$ is

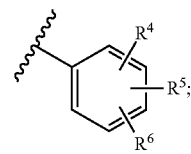

wherein $R^4$ is $C_{1-6}$alkoxy or carboxy;
$R^5$ is hydrogen or $C_{1-6}$alkoxy;
$R^6$ is hydrogen or $C_{1-6}$alkoxy;
Q is

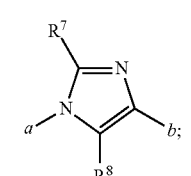

wherein one of $R^7$ and $R^8$ is $C_{1-6}$alkyl, and the other one is hydrogen.

Further embodiment of present invention is (iv) a compound of formula I or a pharmaceutically acceptable salt thereof, wherein $R^1$ is methyl, chloro or bromo;
$R^2$ is hydrogen or methyl;
$R^3$ is

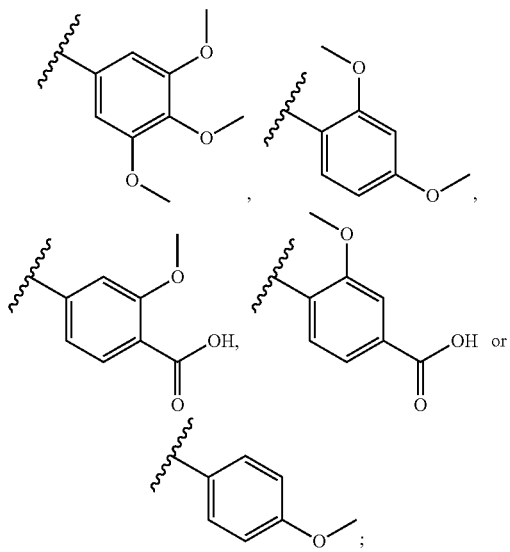

Q is

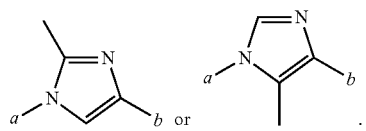

Another embodiment of present invention is (v) a compound of formula I or a pharmaceutically acceptable salt thereof, wherein $R^1$ is $C_{1-6}$alkyl or halogen;
$R^2$ is hydrogen or $C_{1-6}$alkyl;
$R^3$ is

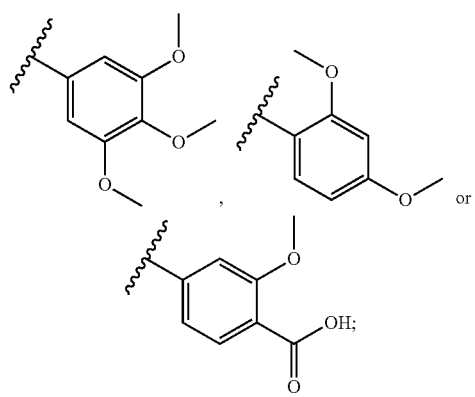

Q is

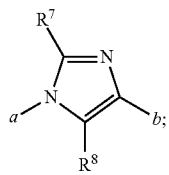

wherein one of $R^7$ and $R^8$ is $C_{1-6}$alkyl, and the other one is hydrogen.

Further embodiment of present invention is (vi) a compound of formula I or a pharmaceutically acceptable salt thereof, wherein $R^1$ is methyl, chloro or bromo;
$R^2$ is hydrogen or methyl;
$R^3$ is

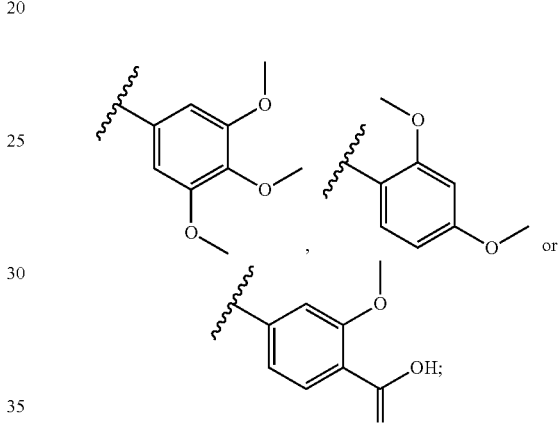

Q is

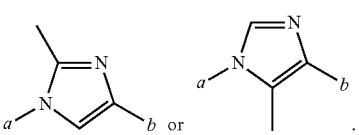

Another embodiment of present invention is (vii) a compound of formula I or a pharmaceutically acceptable salt thereof, wherein $R^1$ is $C_{1-6}$alkoxy or halogen;
$R^2$ is hydrogen;
$R^3$ is

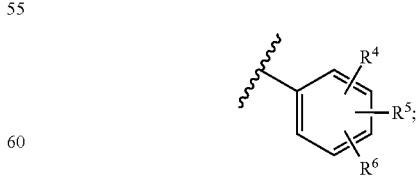

wherein $R^4$ is $C_{1-6}$ alkoxy, $C_{1-6}$ alkoxycarbonyl, carboxy or halogen;
$R^5$ is hydrogen, $C_{1-6}$alkyl or $C_{1-6}$alkoxy;
$R^6$ is hydrogen or $C_{1-6}$alkoxy;

Q is

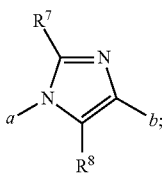

wherein $R^7$ is $C_{1-6}$alkyl, hydroxy-$CH_2$— or halogen;

$R^8$ is $C_{1-6}$alkyl.

Further embodiment of present invention is (viii) a compound of formula I or a pharmaceutically acceptable salt thereof, wherein $R^1$ is methoxy, chloro or bromo;

$R^2$ is hydrogen;

$R^3$ is

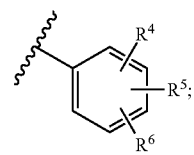

wherein $R^4$ is methoxy, methoxycarbonyl, carboxy or fluoro;

$R^5$ is hydrogen, methyl or methoxy;

$R^6$ is hydrogen or methoxy;

Q is

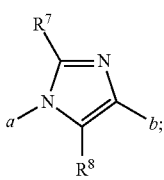

wherein $R^7$ is methyl, hydroxy-$CH_2$— or bromo;

$R^8$ is methyl.

Another embodiment of present invention is (ix) a compound of formula I or a pharmaceutically acceptable salt thereof, wherein $R^1$ is halogen;

$R^2$ is hydrogen;

$R^3$ is

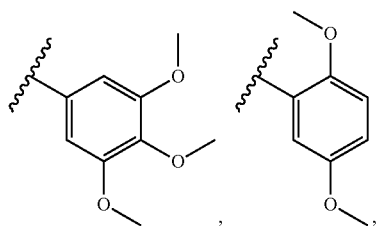

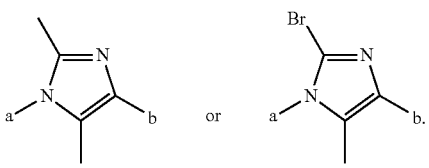

Q is

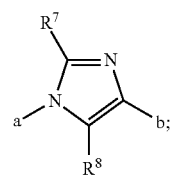

wherein $R^7$ is $C_{1-6}$alkyl or halogen;

$R^8$ is $C_{1-6}$alkyl.

Further embodiment of present invention is (x) a compound of formula I or a pharmaceutically acceptable salt thereof, wherein $R^1$ is chloro or bromo;

$R^2$ is hydrogen;

$R^3$ is

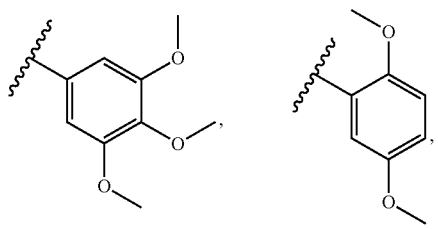

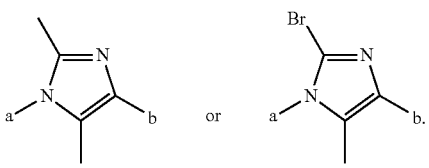

Q is

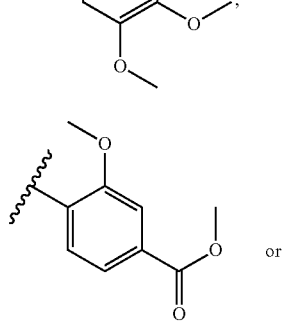

Particular compounds of formula I, including their activity data, NMR data and MS data are summarized in the following Table 1 and 2.

TABLE 1

Structure, name and activity data of particular compounds

| Example No. | Structure | Name | CPE_EC$_{50}$ (μM, Long Strain) |
|---|---|---|---|
| 1-1 | 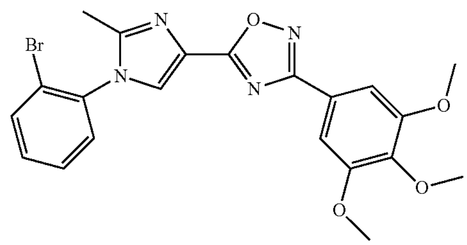 [SMILES: COc1cc(-c2noc(-c3cn(-c4ccccc4Br)c(C)n3)n2)cc(OC)c1OC] | 5-(1-(2-Bromophenyl)-2-methyl-1H-imidazol-4-yl)-3-(3,4,5-trimethoxyphenyl)-1,2,4-oxadiazole | 0.78 |
| 1-2 | 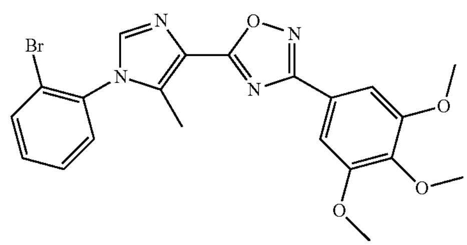 [SMILES: COc1cc(-c2noc(-c3ncn(-c4ccccc4Br)c3C)n2)cc(OC)c1OC] | 5-[1-(2-Bromo-phenyl)-5-methyl-1H-imidazol-4-yl]-3-(3,4,5-trimethoxy-phenyl)-[1,2,4]oxadiazole | 0.6 |
| 1-3 | 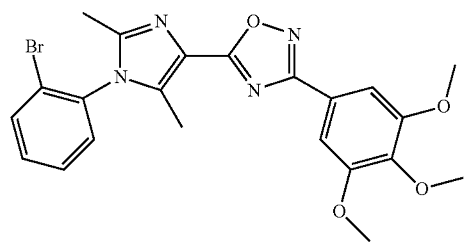 [SMILES: COc1cc(-c2noc(-c3nc(C)n(-c4ccccc4Br)c3C)n2)cc(OC)c1OC] | 5-(1-(2-Bromophenyl)-2,5-dimethyl-1H-imidazol-4-yl)-3-(3,4,5-trimethoxyphenyl)-1,2,4-oxadiazole | 0.5 |
| 1-4 | 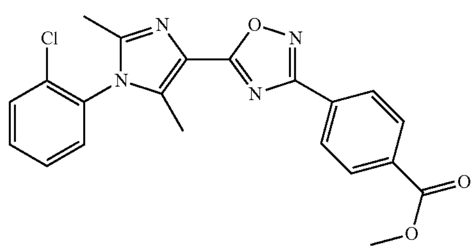 [SMILES: COC(=O)c1ccc(-c2noc(-c3nc(C)n(-c4ccccc4Cl)c3C)n2)cc1] | 4-{5-[1-(2-Chloro-phenyl)-2,5-dimethyl-1H-imidazol-4-yl]-[1,2,4]oxadiazol-3-yl}-benzoic acid methyl ester | 4.06 |
| 1-5 | 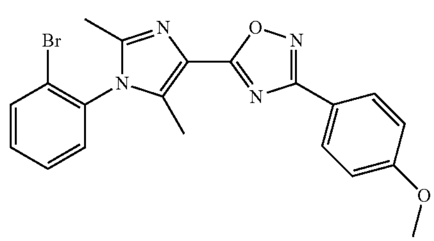 [SMILES: COc1ccc(-c2noc(-c3nc(C)n(-c4ccccc4Br)c3C)n2)cc1] | 5-[1-(2-Chlorophenyl)-2,5-dimethyl-1H-imidazol-4-yl]-3-(4-methoxy-phenyl)-[1,2,4]oxadiazole | 2 |
| 1-6 | 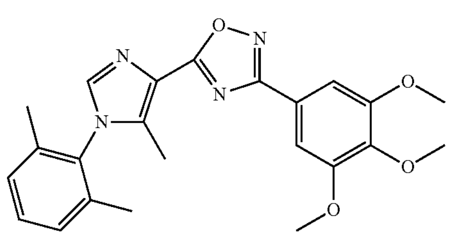 [SMILES: COc1cc(-c2noc(-c3ncn(-c4c(C)cccc4C)c3C)n2)cc(OC)c1OC] | 5-(1-(2,6-Dimethylphenyl)-5-methyl-1H-imidazol-4-yl)-3-(3,4,5-trimethoxyphenyl)-1,2,4-oxadiazole | 0.51 |

TABLE 1-continued

Structure, name and activity data of particular compounds

| Example No. | Structure | Name | CPE_EC$_{50}$ (µM, Long Strain) |
|---|---|---|---|
| 1-7 | 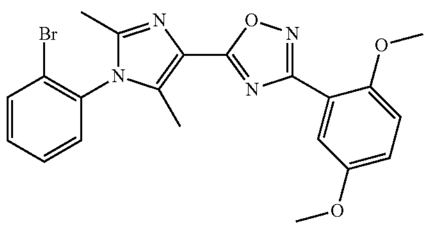 [SMILES: COc1ccc(OC)c(-c2noc(-c3nc(C)n(-c4ccccc4Br)c3C)n2)c1] | 5-[1-(2-Bromo-phenyl)-2,5-dimethyl-1H-imidazol-4-yl]-3-(2,5-dimethoxy-phenyl)-[1,2,4]oxadiazole | 0.68 |
| 1-8 | 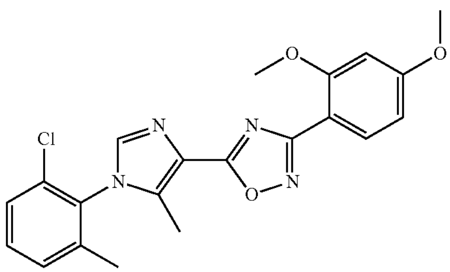 [SMILES: COc1ccc(-c2noc(-c3ncn(-c4c(C)cccc4Cl)c3C)n2)c(OC)c1] | 5-[1-(2-Chloro-6-methyl-phenyl)-5-dimethyl-1H-imidazol-4-yl]-3-(2,4-dimethoxy-phenyl)-[1,2,4]oxadiazole | 0.193 |
| 1-9 | 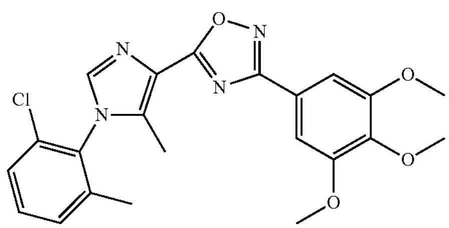 [SMILES: COc1cc(-c2noc(-c3ncn(-c4c(C)cccc4Cl)c3C)n2)cc(OC)c1OC] | 5-[1-(2-Chloro-6-methyl-phenyl)-5-methyl-imidazol-4-yl]-3-(3,4,5-trimethoxyphenyl)-1,2,4-oxadiazole | 0.22 |
| 1-10 | 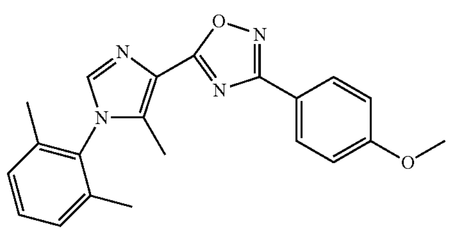 [SMILES: COc1ccc(-c2noc(-c3ncn(-c4c(C)cccc4C)c3C)n2)cc1] | 5-(1-(2,6-Dimethylphenyl)-5-methyl-1H-imidazol-4-yl)-3-(4-methoxyphenyl)-1,2,4-oxadiazol | 2.4 |
| 1-11 | 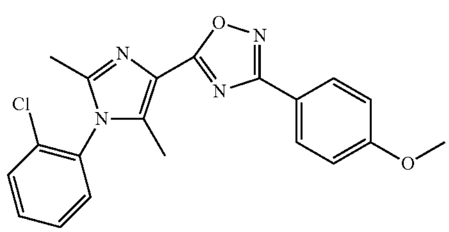 [SMILES: COc1ccc(-c2noc(-c3nc(C)n(-c4ccccc4Cl)c3C)n2)cc1] | 5-[1-(2-Chloro-phenyl)-2,5-dimethyl-1H-imidazol-4-yl]-3-(4-methoxy-phenyl)-[1,2,4]oxadiazole | 5.07 |
| 1-12 | 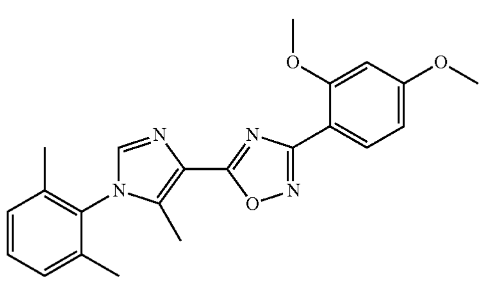 [SMILES: COc1ccc(-c2noc(-c3ncn(-c4c(C)cccc4C)c3C)n2)c(OC)c1] | 3-(2,4-Dimethoxy-phenyl)-5-[1-(2,6-dimethyl-phenyl)-5-methyl-1H-imidazol-4-yl]-[1,2,4]oxadiazole | 0.362 |

TABLE 1-continued

Structure, name and activity data of particular compounds

| Example No. | Structure | Name | CPE_EC$_{50}$ (µM, Long Strain) |
|---|---|---|---|
| 1-13 | 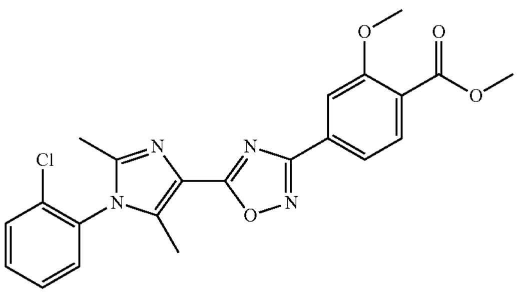 [SMILES: COC(=O)c1ccc(-c2noc(-c3nc(C)n(-c4ccccc4Cl)c3C)n2)cc1OC] | 4-{5-[1-(2-Chloro-phenyl)-2,5-dimethyl-1H-imidazol-4-yl]-[1,2,4]oxadiazol-3-yl}-2-methoxy-benzoic acid methyl ester | 2.38 |
| 1-14 | 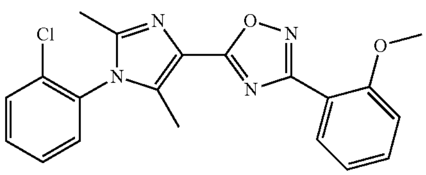 [SMILES: COc1ccccc1-c1noc(-c2nc(C)n(-c3ccccc3Cl)c2C)n1] | 5-[1-(2-Chloro-phenyl)-2,5-dimethyl-1H-imidazol-4-yl]-3-(2-methoxy-phenyl)-[1,2,4]oxadiazole | 0.68 |
| 1-15 | 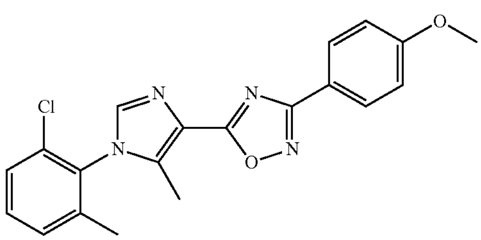 [SMILES: COc1ccc(-c2noc(-c3ncn(-c4c(C)cccc4Cl)c3C)n2)cc1] | 5-[1-(2-Chloro-6-methyl-phenyl)-5-methyl-1H-imidazol-4-yl]-3-(4-methoxy-phenyl)-[1,2,4]oxadiazole | 1.738 |
| 1-16 | 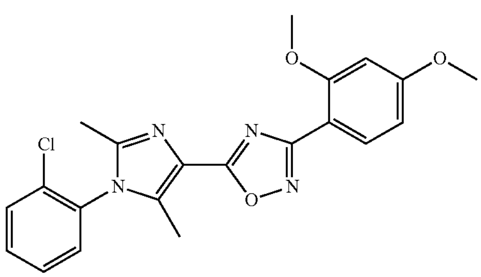 [SMILES: COc1ccc(-c2noc(-c3nc(C)n(-c4ccccc4Cl)c3C)n2)c(OC)c1] | 5-[1-(2-Chloro-phenyl)-2,5-dimethyl-1H-imidazol-4-yl]-3-(2,4-dimethoxy-phenyl)-[1,2,4]oxadiazole | 1.467 |
| 1-17 | 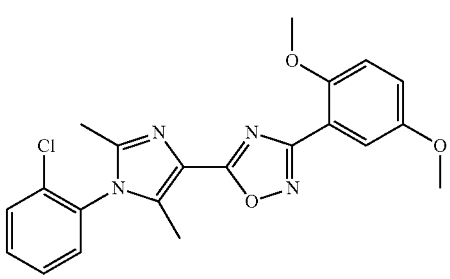 [SMILES: COc1ccc(OC)c(-c2noc(-c3nc(C)n(-c4ccccc4Cl)c3C)n2)c1] | 5-(1-(2-chlorophenyl)-2,5-dimethyl-1H-imidazol-4-yl)-3-(2,5-dimethoxy-phenyl)-1,2,4-oxadiazole | 1.814 |

TABLE 1-continued

Structure, name and activity data of particular compounds

| Example No. | Structure | Name | CPE_EC$_{50}$ (µM, Long Strain) |
|---|---|---|---|
| 1-18 | 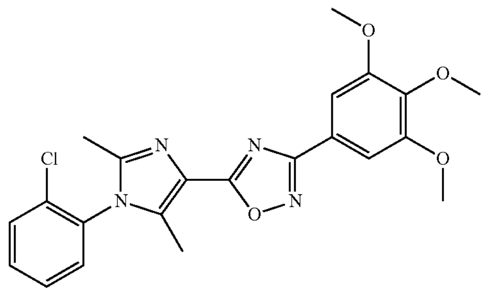 [SMILES: COc1cc(-c2noc(-c3nc(C)n(-c4ccccc4Cl)c3C)n2)cc(OC)c1OC] | 5-[1-(2-Chloro-phenyl)-2,5-dimethyl-1H-imidazol-4-yl]-3-(3,4,5-trimethoxy-phenyl)-[1,2,4]oxadiazole | 1.59 |
| 1-19 | 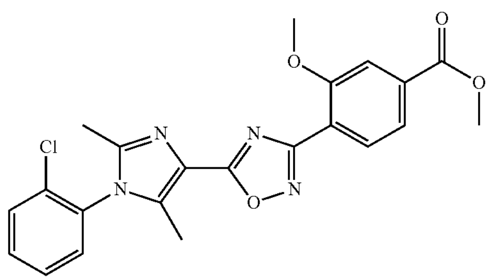 [SMILES: COC(=O)c1ccc(-c2noc(-c3nc(C)n(-c4ccccc4Cl)c3C)n2)c(OC)c1] | 4-{5-[1-(2-Chloro-phenyl)-2,5-dimethyl-1H-imidazol-4-yl]-[1,2,4]oxadiazol-3-yl}-3-methoxy-benzoic acid methyl ester | 0.92 |
| 1-20 | 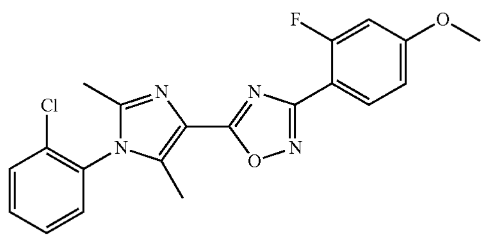 [SMILES: COc1ccc(-c2noc(-c3nc(C)n(-c4ccccc4Cl)c3C)n2)c(F)c1] | 5-[1-(2-Chloro-phenyl)-2,5-dimethyl-1H-imidazol-4-yl]-3-(2-fluoro-4-methoxy-phenyl)-[1,2,4]oxadiazole | 2.99 |
| 1-21 | 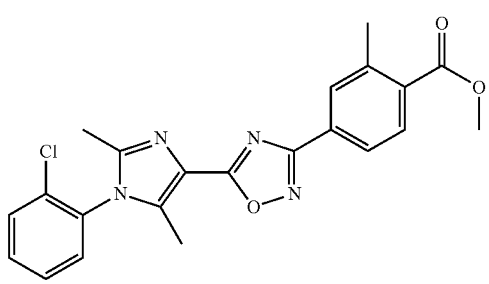 [SMILES: COC(=O)c1ccc(-c2noc(-c3nc(C)n(-c4ccccc4Cl)c3C)n2)cc1C] | 4-{5-[1-(2-Chloro-phenyl)-2,5-dimethyl-1H-imidazol-4-yl]-[1,2,4]oxadiazol-3-yl}-2-methyl-benzoic acid methyl ester | 5.31 |
| 1-22 | 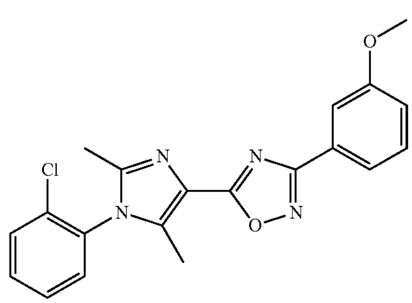 [SMILES: COc1cccc(-c2noc(-c3nc(C)n(-c4ccccc4Cl)c3C)n2)c1] | 5-[1-(2-Chloro-phenyl)-2,5-dimethyl-1H-imidazol-4-yl]-3-(3-methoxy-phenyl)-[1,2,4]oxadiazole | 5.96 |

TABLE 1-continued

Structure, name and activity data of particular compounds

| Example No. | Structure | Name | CPE_EC$_{50}$ (µM, Long Strain) |
|---|---|---|---|
| 1-23 | 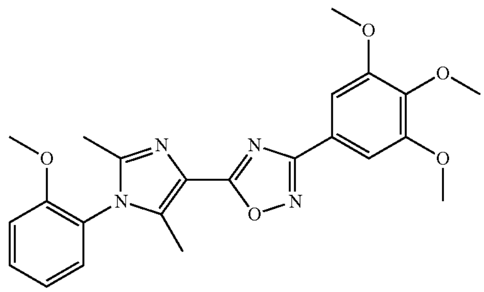 [SMILES: COc1ccccc1-n1c(C)nc(-c2nc(-c3cc(OC)c(OC)c(OC)c3)no2)c1C] | 5-[1-(2-Methoxy-phenyl)-2,5-dimethyl-1H-imidazol-4-yl]-3-(3,4,5-trimethoxy-phenyl)-[1,2,4]oxadiazole | 2.084 |
| 1-24 | 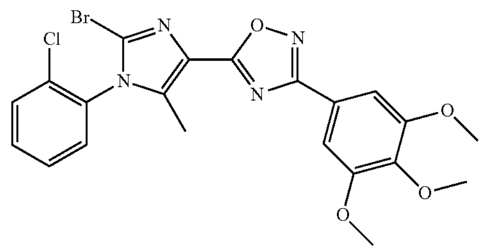 [SMILES: COc1cc(-c2noc(-c3nc(Br)n(-c4ccccc4Cl)c3C)n2)cc(OC)c1OC] | 5-[2-Bromo-1-(2-chloro-phenyl)-5-methyl-1H-imidazol-4-yl]-3-(3,4,5-trimethoxy-phenyl)-[1,2,4]oxadiazole | 0.78 |
| 1-25 | 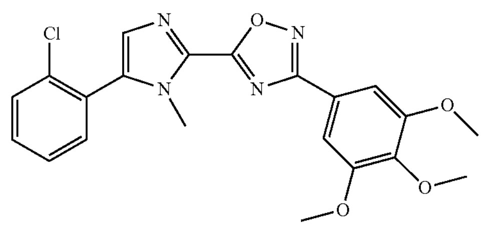 [SMILES: COc1cc(-c2noc(-c3ncc(-c4ccccc4Cl)n3C)n2)cc(OC)c1OC] | 5-[5-(2-Chlorophenyl)-1-methyl-imidazol-2-yl]-3-(3,4,5-trimethoxyphenyl)-1,2,4-oxadiazole | 1.28 |
| 1-26 | 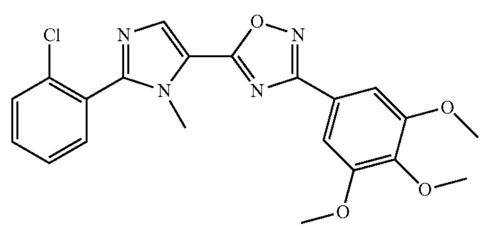 [SMILES: COc1cc(-c2noc(-c3cnc(-c4ccccc4Cl)n3C)n2)cc(OC)c1OC] | 5-[2-(2-Chlorophenyl)-3-methyl-imidazol-4-yl]-3-(3,4,5-trimethoxyphenyl)-1,2,4-oxadiazole | 2.03 |
| 2-1 | 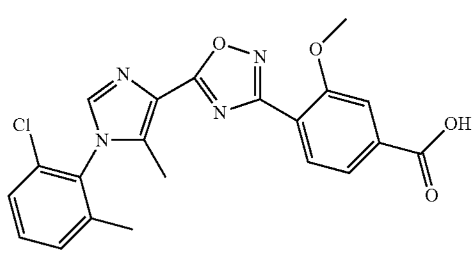 [SMILES: COc1cc(C(=O)O)ccc1-c1noc(-c2ncn(-c3c(C)cccc3Cl)c2C)n1] | 4-[5-[1-(2-Chloro-6-methyl-phenyl)-5-methyl-imidazol-4-yl]-1,2,4-oxadiazol-3-yl]-3-methoxy-benzoic acid | 1.85 |
| 2-2 | 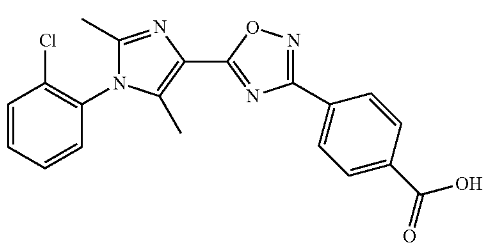 [SMILES: Cc1nc(-c2nc(-c3ccc(C(=O)O)cc3)no2)c(C)n1-c1ccccc1Cl] | 4-{5-[1-(2-Chloro-phenyl)-2,5-dimethyl-1H-imidazol-4-yl]-[1,2,4]oxadiazol-3-yl}-benzoic acid | 3.08 |

TABLE 1-continued

Structure, name and activity data of particular compounds

| Example No. | Structure | Name | CPE_EC$_{50}$ (μM, Long Strain) |
|---|---|---|---|
| 2-3 | 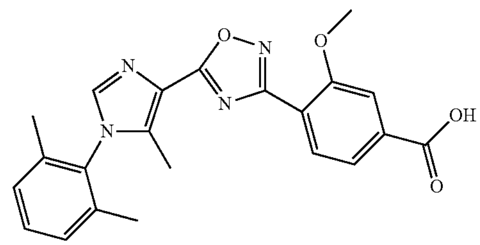 | 4-{5-[1-(2,6-Dimethyl-phenyl)-5-methyl-1H-imidazol-4-yl]-[1,2,4]oxadiazol-3-yl}-3-methoxy-benzoic acid | 1.97 |
| 2-4 | 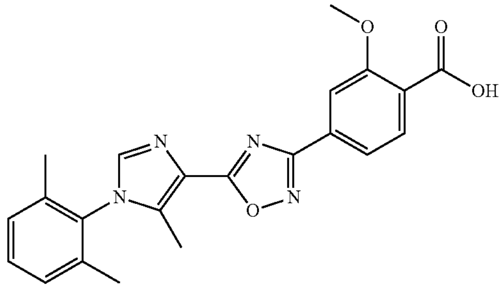 [SMILES: COc1cc(-c2noc(-c3ncn(-c4c(C)cccc4C)c3C)n2)ccc1C(=O)O] | 4-{5-[1-(2,6-Dimethyl-phenyl)-5-methyl-1H-imidazol-4-yl]-[1,2,4]oxadiazol-3-yl}-2-methoxy-benzoic acid | 0.76 |
| 2-5 | 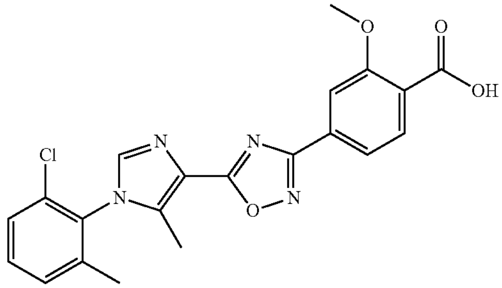 | 4-{5-[1-(2-Chloro-6-methyl-phenyl)-5-methyl-1H-imidazol-4-yl]-[1,2,4]oxadiazol-3-yl}-2-methoxy-benzoic acid | 0.59 |
| 3-1 | 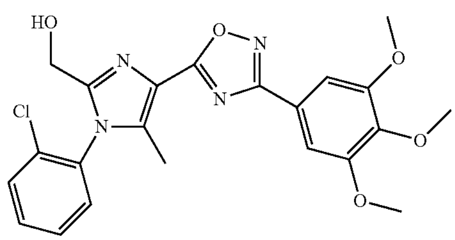 [SMILES: COc1cc(-c2noc(-c3nc(CO)n(-c4ccccc4Cl)c3C)n2)cc(OC)c1OC] | (1-(2-Chlorophenyl)-5-methyl-4-(3-(3,4,5-trimethoxyphenyl)-1,2,4-oxadiazol-5-yl)-1H-imidazol-2-yl)methanol | 1.79 |
| 3-2 | 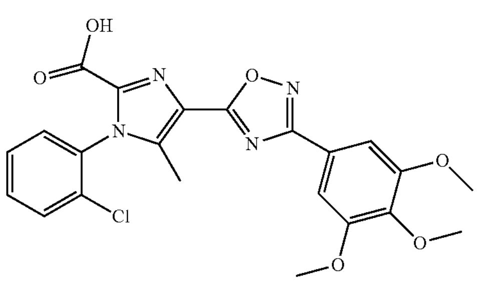 [SMILES: COc1cc(-c2noc(-c3nc(C(=O)O)n(-c4ccccc4Cl)c3C)n2)cc(OC)c1OC] | 1-(2-Chlorophenyl)-5-methyl-4-(3-(3,4,5-trimethoxyphenyl)-1,2,4-oxadiazol-5-yl)-1H-imidazole-2-carboxylic acid | 4.05 |

TABLE 2

NMR and MS data of particular compounds

| Example No. | $^1$H NMR data | MW data |
|---|---|---|
| 1-1 | $^1$H NMR (400 MHz, DMSO-$d_6$) δ ppm 8.42 (s, 1 H), 7.94-7.92 (m, 1 H), 7.71-7.54 (m, 3 H), 7.34 (s, 2 H), 3.89 (s, 6 H), 3.75 (s, 3 H), 2.20 (s, 3 H) | MS obsd. (ESI$^+$) [(M + H)$^+$] 471 |
| 1-2 | $^1$H NMR (400 MHz, MeOH-$d_4$) δ ppm 7.96 (s, 1 H), 7.94-7.92 (m, 1 H), 7.66-7.58 (m, 3 H), 7.49 (s, 2 H), 3.96 (s, 6 H), 3.86 (s, 3 H), 2.53 (s, 3 H) | MS obsd. (ESI$^+$) [(M + H)$^+$] 471 |
| 1-3 | $^1$H NMR (400 MHz, DMSO-$d_6$) δ ppm 7.98 (d, J = 8.4 Hz, 1 H), 7.70-7.69 (m, 2 H), 7.62-7.60 (m, 1 H), 7.36 (s, 2H), 3.89 (s, 6 H), 3.76 (s, 3 H), 2.37 (s, 3 H), 2.14 (s, 3H) | MS obsd. (ESI$^+$) [(M + H)$^+$] 485 |
| 1-4 | $^1$H NMR (400 MHz, MeOH-$d_4$) δ ppm 8.32 (d, J = 8.0 Hz, 2 H), 8.18 (d, J = 8.0 Hz, 2 H), 7.65-7.71 (m, 1 H), 7.50-7.61 (m, 2 H), 7.34-7.40 (m, 1 H), 3.98 (s, 3 H), 2.46 (s, 3 H), 2.28 (s, 3 H) | MS obsd. (ESI$^+$) [(M + H)$^+$] 409 |
| 1-5 | $^1$H NMR (400 MHz, DMSO-$d_6$) δ ppm 8.16 (d, J = 8.0 Hz, 2H), 7.83 (dd, J = 1.2, 8.0 Hz, 1H), 7.55 (dt, J = 1.2, 8.0 Hz, 1H), 7.46 (dt, J = 1.6, 8.0 Hz, 1H), 7.35 (dd, J = 1.6, 8.0 Hz, 1H), 7.01 (d, J = 8.0 Hz, 2H), 3.87 (s, 3H), 2.42 (s, 3H), 2.25 (s, 3H) | MS obsd. (ESI$^+$) [(M + H)$^+$] 425 |
| 1-6 | $^1$H NMR (400 MHz, DMSO-$d_6$) δ ppm 7.93 (s, 1 H), 7.40-7.36 (m, 1 H), 7.33-7.29 (m, 4 H), 3.86 (s, 6 H), 3.72 (s, 3 H), 2.33 (s, 6 H), 1.95 (s, 3 H) | MS obsd. (ESI$^+$) [(M + H)$^+$] 421 |
| 1-7 | $^1$H NMR (400 MHz, CDCl$_3$) δ ppm 7.80-7.83 (m, 2H), 7.54 (dt, J = 1.6, 8.0 Hz, 1H), 7.45 (dt, J = 1.6, 8.0 Hz, 1H), 7.34 (dd, J = 1.6, 8.0 Hz, 1H), 7.00-7.02 (m, 2H), 3.96 (s, 3H), 3.85 (s, 3H), 2.40 (s, 3H), 2.24 (s, 3H) | MS obsd. (ESI$^+$) [(M + H)$^+$] 456 |
| 1-8 | $^1$H NMR (400 MHz, MeOH-$d_4$) δ ppm 8.08-8.10 (m, 1H), 7.90 (s, 1H), 7.44-7.55 (m, 3H), 6.67-6.71(m, 2H), 3.95 (s, 3H), 3.88(s, 3H), 2.44 (s, 3H), 2.13 (s, 3H) | MS obsd. (ESI$^+$) [(M + H)$^+$] 411 |
| 1-9 | $^1$H NMR (400 MHz, MeOH-$d_4$) δ ppm 7.92 (s, 1 H), 7.52-7.58 (m, 2 H), 7.40-7.50 (m, 3 H), 3.94 (s, 6 H), 3.85 (s, 3 H), 2.47 (s, 3 H), 2.15 (s, 3H) | MS obsd. (ESI$^+$) [(M + H)$^+$] 441 |
| 1-10 | $^1$H NMR (400 MHz, DMSO-$d_6$) δ ppm 8.10-8.08 (m, 2 H), 7.86 (s, 1 H), 7.43-7.39 (m, 1 H), 7.33-7.31 (m, 2 H), 7.10-7.07 (m, 2H), 3.89 (s, 3 H), 2.43 (s, 3 H), 2.05 (s, 6 H) | MS obsd. (ESI$^+$) [(M + H)$^+$] 361 |
| 1-11 | $^1$H NMR (400 MHz, DMSO-$d_6$) δ ppm 8.2 (d, J = 8.0 Hz, 2H), 7.85 (d, J = 8.0 Hz, 1H), 7.69 (m, 3H), 7.14 (d, J = 8.0 Hz, 2H), 3.85 (s, 3H), 2.38 (s, 3H), 2.14 (s, 3H) | MS obsd. (ESI$^+$) [(M + H)$^+$] 381 |
| 1-12 | $^1$H NMR (400 MHz, MeOH-$d_4$) δ ppm 8.08 (d, J = 8.8 Hz, 1 H), 7.84 (s, 1 H), 7.40-7.29 (m, 3 H), 6.71-6.67 (m, 2 H), 3.95 (s, 3 H), 3.88 (s, 3 H), 2.41 (s, 3 H), 2.03 (s, 6 H) | MS obsd. (ESI$^+$) [(M + H)$^+$] 390.9 |
| 1-13 | $^1$H NMR (400 MHz, CDCl$_3$) δ ppm 7.93 (m, 1H), 7.86 (m, 2H), 7.69 (m, 3H), 7.39 (d, J = 4.0 Hz, 1H), 4.04 (s, 3H), 3.95 (s, 3H), 2.45 (s, 3H), 2.31 (s, 3H) | MS obsd. (ESI$^+$) [(M + H)$^+$] 439 |
| 1-14 | $^1$H NMR (400 MHz, CDCl$_3$) δ ppm 8.28 (d, J = 4.0 Hz, 1H), 7.68 (m, 1H), 7.50 (m, 3H), 7.36 (d, J = 8.0 Hz, 1H), 7.09 (m, 2H), 4.03 (s, 3H), 2.43 (s, 3H), 2.28 (s, 3H) | MS obsd. (ESI$^+$) [(M + H)$^+$] 381.0 |
| 1-15 | $^1$H NMR (400 MHz, MeOH-$d_4$) δ ppm 8.07 (d, J = 8.8 Hz, 2 H), 7.89 (s, 1H), 7.55-7.44 (m, 3 H), 7.06 (d, J = 9.2 Hz, 2 H), 3.87 (s, 3 H), 2.45 (s, 3 H), 2.13 (s, 3 H) | MS obsd. (ESI+) [(M + H)$^+$] 381.0 |
| 1-16 | $^1$H NMR (400 MHz, DMSO-$d_6$) δ ppm 7.92 (d, J = 8.0 Hz, 1H), 7.84 (d, J = 8.0 Hz, 3 H), 7.30-7.40 (m, 1H), 6.70-6.75(m, 2H), 3.90 (s, 3H), 2.14 (s, 3H), 3.86 (s, 3H), 2.35 (s, 3H) | MS obsd. (ESI$^+$) [(M + H)$^+$] 411 |
| 1-17 | $^1$H NMR (400 MHz, MeOH-$d_4$) δ ppm 8.08 (d, J = 8.4 Hz, 1 H), 7.90 (s, 1H), 7.55-7.44 (m, 3 H), 6.71-6.67 (m, 2 H), 3.95 (s, 3 H), 3.88 (s, 3 H), 2.44 (s, 3 H), 2.13 (s, 3 H) | MS obsd. (ESI$^+$) [(M + H)$^+$] 410.8 |
| 1-18 | $^1$H NMR (400 MHz, DMSO-$d_6$) δ ppm 7.83 (d, J = 8.0 Hz, 1H), 7.61-7.72 (m, 3H), 7.36(s, 2H), 3.88 (s, 6H), 3.75 (s, 3H), 2.38 (s, 3H), 2.12 (s, 3H) | MS obsd. (ESI$^+$) [(M + H)$^+$] 441 |
| 1-19 | $^1$H NMR (400 MHz, MeOH-$d_4$) δ ppm 7.82 (d, J = 8.0 Hz, 1H), 7.77-7.82 (m, 3H), 7.51-7.62 (m, 3H), 4.06 (s, 3H), 3.98 (s, 3H), 2.47 (s, 3H), 2.27 (s, 3H) | MS obsd. (ESI$^+$) [(M + H)$^+$] 439 |
| 1-20 | $^1$H NMR (400 MHz, DMSO-$d_6$) δ ppm 7.83 (t, J = 8.0 Hz, 1H), 7.72 (d, J = 8.0 Hz, 1H), 7.61-7.75 (m, 3H), 7.09 (d, J = 12 Hz, 1H), 7.01 (d, J = 8.0 Hz, 1H), 3.87 (s, 3H), 2.37 (s, 3H), 2.15 (s, 3H) | MS obsd. (ESI$^+$) [(M + H)$^+$] 399 |
| 1-21 | $^1$H NMR (400 MHz, DMSO-$d_6$) δ ppm 7.85 (d, J = 8.0 Hz, 2H), 7.84 (s, 1H), 7.74 (d, J = 4.0 Hz, 1H), 7.61-7.73 (m, 3H), 3.88 (s, 3H), 2.62 (s, 3H), 2.39 (s, 3H), 2.15 (s, 3H) | MS obsd. (ESI$^+$) [(M + H)$^+$] 423 |
| 1-22 | $^1$H NMR (400 MHz, CDCl$_3$) δ ppm 7.82 (d, J = 8.0 Hz, 1H), 7.78 (m, 1H), 7.52 (d, J = 4.0 Hz, 1H), 7.51 (m, 2H), 7.41 (t, J = 8.0 Hz, 1H), 7.37 (dd, J = 8.0, 4.0 Hz, 1H), 7.07 (d, J = 8.0 Hz, 1H), 3.91 (s, 3H), 2.45 (s, 3H), 2.28 (s, 3H) | MS obsd. (ESI$^+$) [(M + H)$^+$] 381 |
| 1-23 | $^1$H NMR (400 MHz, CDCl$_3$) δ ppm 7.55 (m, 1H), 7.51 (s, 2H), 7.22 (d, J = 8.0, 4.0 Hz, 1H), 7.15 (t, J = 8.0 Hz, 2H), 4.01(s, 6H), 3.96(s, 3H), 3.84 (s, 3H), 2.42 (s, 3H), 2.26 (s, 3H) | MS obsd. (ESI$^+$) [(M + H)$^+$] 437 |
| 1-24 | $^1$H NMR (400 MHz, CDCl$_3$) δ ppm 7.58 (dt, J = 1.6, 8.0 7.52 (dt, J = 1.6, 8.0 Hz, 1H), 7.45 (s, 2H), 7.37 (dd, J = 1.6, 8.0 Hz, 1H), 3.95 (s, 6H), 3.91 (s, 3H), 2.48 (s, 3H) | MS obsd. (ESI$^+$) [(M + H)$^+$] 506 |

TABLE 2-continued

NMR and MS data of particular compounds

| Example No. | $^1$H NMR data | MW data |
|---|---|---|
| 1-25 | $^1$H NMR (400 MHz, CDCl$_3$) δ ppm 7.57-7.59 (m, 1 H), 7.46-7.48 (m, 1 H), 7.41-7.42 (m, 2 H), 7.37-7.41 (m, 2H), 7.26 (s, 1H), 3.99 (s, 3 H), 3.97 (s, 6H), 3.93 (s, 3 H) | MS obsd. (ESI$^+$) [(M + H)$^+$] 427 |
| 1-26 | $^1$H NMR (400 MHz, CDCl$_3$) δ ppm 8.10 (s, 1 H), 7.39-7.56 (m, 4 H), 7.26 (s, 2 H), 3.96 (s, 3 H), 3.94 (s, 6 H), 3.92 (s, 3 H) | MS obsd. (ESI$^+$) [(M + H)$^+$] 427 |
| 2-1 | $^1$H NMR (400 MHz, MeOH-d$_4$) δ ppm 8.21 (d, J = 8 Hz, 1H), 7.93 (s, 1H), 7.82 (m, 1H), 7.78 (s, J = 6.8 Hz, 1H), 7.48-7.57 (m, 3H), 4.04 (s, 3H), 2.48 (s, 3H), 2.15 (s, 3H) | MS obsd. (ESI$^+$) [(M + H)$^+$] 425 |
| 2-2 | $^1$H NMR (400 MHz, MeOH-d$_4$) δ ppm 8.27 (d, J = 8.0 Hz, 2 H), 8.20 (d, J = 8.0 Hz, 2 H), 7.79-7.81 (m, 1 H), 7.60-7.71 (m, 3 H), 2.48 (s, 3 H), 2.24 (s, 3 H) | MS obsd. (ESI+) [(M + H)$^+$] 393 |
| 2-3 | $^1$H NMR (400 MHz, CDCl$_3$) δ ppm 8.22 (d, J = 8 Hz, 1 H), 7.88 (s, 1 H), 7.83 (s, 1H), 7.78 (d, J = 8 Hz, 1 H), 7.39-7.43 (s, 1 H), 7.31-7.33 (m, 1 H), 7.25 (s, 1 H), 4.05 (s, 3 H), 2.44 (s, 3 H), 2.05 (s, 6 H) | MS obsd. (ESI$^+$) [(M + H)$^+$] 405 |
| 2-4 | $^1$H NMR (400 MHz, CDCl$_3$) δ ppm 8.34 (d, 1 H), 8.00-8.04 (m, 2 H), 7.96 (s, 1 H), 7.59 (s, 1 H), 7.35-7.39 (m, 1 H), 7.25 (s, 1 H), 4.22 (s, 3 H), 2.44 (s, 3 H), 2.05 (s, 6 H) | MS obsd. (ESI$^+$) [(M + H)$^+$] 405 |
| 2-5 | $^1$H NMR (400 MHz, CDCl$_3$) δ ppm 8.34 (d, 1 H), 8.01 (d, 1 H), 7.96 (s, 1 H), 7.60 (s, 1 H), 7.41-7.49 (m, 2H), 7.35 (d, 1H), 4.22 (s, 3 H), 2.48 (s, 3H), 2.13 (s, 3 H) | MS obsd. (ESI$^+$) [(M + H)$^+$] 425 |
| 3-1 | $^1$H NMR (400 MHz, CDCl$_3$) δ ppm 7.81-7.79 (m, 1 H), 7.68-7.60 (m, 3 H), 7.35 (s, 2 H), 5.35 (t, J = 5.6 Hz, 1 H), 4.40-4.35 (m, 1 H), 4.24-4.20 (m, 1 H), 3.89 (s, 6 H), 3.75 (s, 3 H), 2.39 (s, 3 H) | MS obsd. (ESI$^+$) [(M + H)$^+$] 457 |
| 3-2 | $^1$H NMR (400 MHz, CDCl$_3$) δ ppm 7.63-7.65 (m, 1 H), 7.48-7.50 (m, 3 H), 7.35 (s, 2 H), 3.87 (s, 6 H), 3.73 (s, 3 H), 2.30 (s, 3 H) | MS obsd. (ESI$^+$) [(M + H)$^+$] 471 |

More particular compounds of formula I include the following:
5-(1-(2-Bromophenyl)-2-methyl-1H-imidazol-4-yl)-3-(3,4,5-trimethoxyphenyl)-1,2,4-oxadiazole;
5-[1-(2-Bromo-phenyl)-5-methyl-1H-imidazol-4-yl]-3-(3,4,5-trimethoxy-phenyl)-[1,2,4]oxadiazole;
5-(1-(2-Bromophenyl)-2,5-dimethyl-1H-imidazol-4-yl)-3-(3,4,5-trimethoxyphenyl)-1,2,4-oxadiazole;
5-(1-(2,6-Dimethylphenyl)-5-methyl-1H-imidazol-4-yl)-3-(3,4,5-trimethoxyphenyl)-1,2,4-oxadiazole;
5-[1-(2-Bromo-phenyl)-2,5-dimethyl-1H-imidazol-4-yl]-3-(2,5-dimethoxy-phenyl)-[1,2,4]oxadiazole;
5-[1-(2-Chloro-6-methyl-phenyl)-5-dimethyl-1H-imidazol-4-yl]-3-(2,4-dimethoxy-phenyl)-[1,2,4]oxadiazole;
5-[1-(2-Chloro-6-methyl-phenyl)-5-methyl-1H-imidazol-4-yl]-3-(3,4,5-trimethoxyphenyl)-1,2,4-oxadiazole;
3-(2,4-Dimethoxy-phenyl)-5-[1-(2,6-dimethyl-phenyl)-5-methyl-1H-imidazol-4-yl]-[1,2,4]oxadiazole;
5-[1-(2-Chloro-phenyl)-2,5-dimethyl-1H-imidazol-4-yl]-3-(2-methoxy-phenyl)-[1,2,4]oxadiazole;
4-{5-[1-(2-Chloro-phenyl)-2,5-dimethyl-1H-imidazol-4-yl]-[1,2,4]oxadiazol-3-yl}-3-methoxy-benzoic acid methyl ester;
5-[2-Bromo-1-(2-chloro-phenyl)-5-methyl-1H-imidazol-4-yl]-3-(3,4,5-trimethoxy-phenyl)-[1,2,4]oxadiazole;
4-{5-[1-(2,6-Dimethyl-phenyl)-5-methyl-1H-imidazol-4-yl]-[1,2,4]oxadiazol-3-yl}-2-methoxy-benzoic acid; and
4-{5-[1-(2-Chloro-6-methyl-phenyl)-5-methyl-1H-imidazol-4-yl]-[1,2,4]oxadiazol-3-yl}-2-methoxy-benzoic acid.

Synthesis

The compounds of the present invention can be prepared by any conventional means. Suitable processes for synthesizing these compounds as well as their starting materials are provided in the schemes below and in the examples. All substituents, in particular, R$^1$ to R$^9$ and Q are as defined above unless otherwise indicated. Furthermore, and unless explicitly otherwise stated, all reactions, reaction conditions, abbreviations and symbols have the meanings well known to a person of ordinary skill in organic chemistry.

General synthetic route for Compound Ia (Scheme 1)

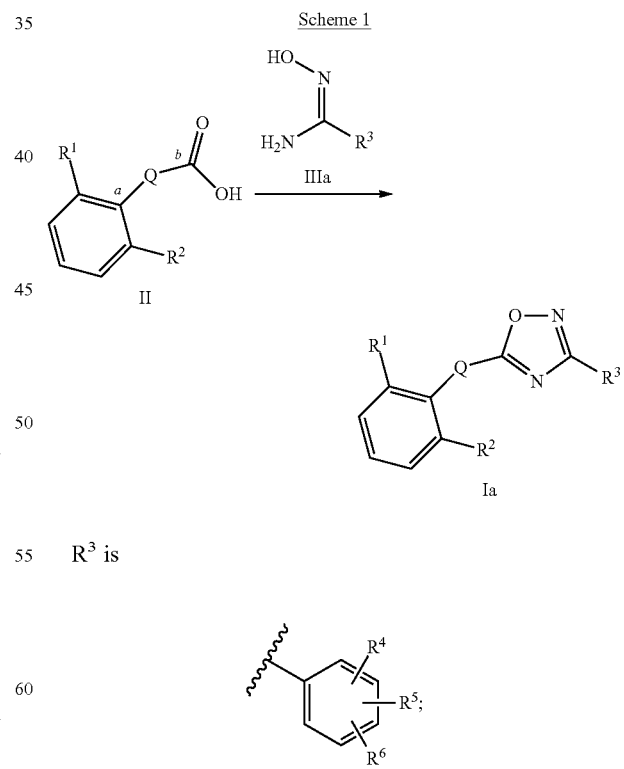

R$^3$ is wherein R$^4$ is C$_{1-6}$alkoxy, C$_{1-6}$alkoxycarbonyl or halogen; R$^5$ is hydrogen, C$_{1-6}$alkyl or C$_{1-6}$alkoxy; R$^6$ is hydrogen or C$_{1-6}$alkoxy;

Q is

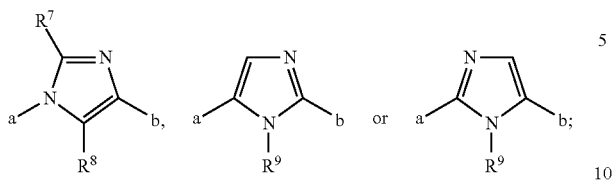

wherein $R^7$ is hydrogen, $C_{1-6}$alkyl or halogen; $R^8$ is hydrogen or $C_{1-6}$alkyl; $R^9$ is $C_{1-6}$alkyl.

Compound of interest Ia can be prepared according to Scheme 1.

Compound Ia can be prepared by cyclization of II with IIIa in the presence of dehydrate reagent such as CDI, DCC in DMF. The reaction can be carried out at 100° C. to 150° C. for several hours or at 150° C. by microwave for several hours.

General synthetic route for Compound Iab (Scheme 2)

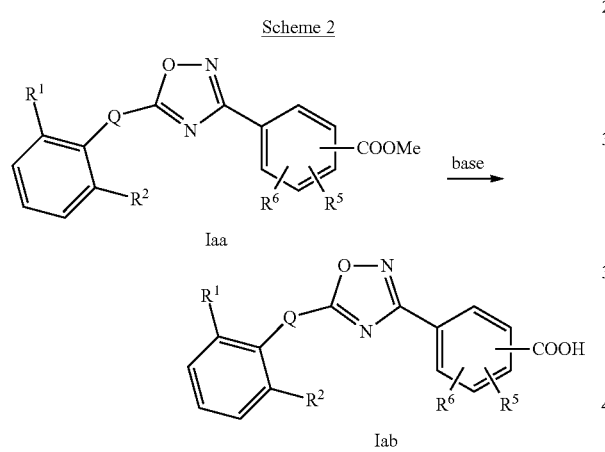

Compound of interest Iab can be prepared according to Scheme 2.

Compound Iab can be prepared by treating Iaa with 10 equiv base such as sodium hydroxide, potassium hydroxide or lithium hydroxide in the mixture of solvent such as THF/H$_2$O, MeOH/H$_2$O at room temperature for several hours or under refluxing for 30 minutes to several hours.

General synthetic route for Compounds Iad and Iae (Scheme 3)

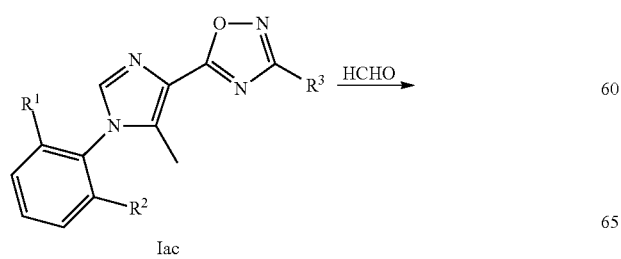

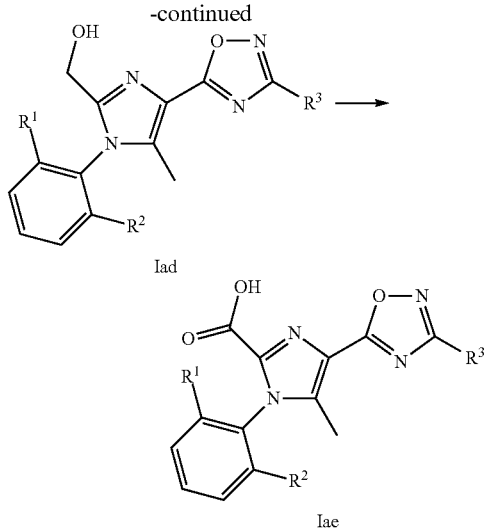

Compounds of interest Iad and Iae can be prepared according to Scheme 3.

Compound Iad can be prepared by reaction of Iac with paraformaldehyde. The reaction can be carried out under microwave. Compound Iae can be prepared by oxidization of Iad. Compound Iad is oxidized with Dess Martin Reagent to give aldehyde. Then it can be oxidization by KMnO$_4$ in K$_2$PO$_4$ solution at room temperature gives Compound Iae.

This invention also relates to a process for the preparation of a compound of formula I comprising the reaction of
(a) a compound of formula (A)

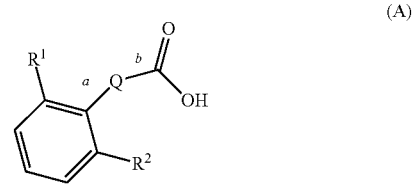

with

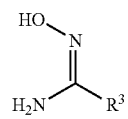

in the presence of a dehydrate reagent;
(b) a compound of formula (B)

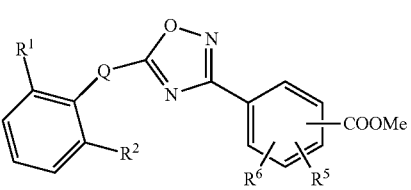

with a base;

(c) a compound of formula (C)

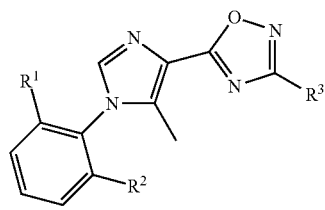

with paraformaldehyde;
(d) a compound of formula (D)

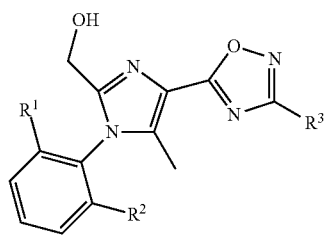

with Dess Martin Reagent and then with KMnO$_4$ in K$_2$PO$_4$; wherein R$^1$ to R$^3$, R$^5$ to R$^6$ and Q are defined above unless otherwise indicated.

In step (a), dehydrate reagent can be for example CDI or DCC;

In step (b), the base can be for example sodium hydroxide, potassium hydroxide or lithium hydroxide.

A compound of formula I when manufactured according to the above process is also an object of the invention.

Pharmaceutical Compositions and Administration

The invention also relates to a compound of formula I for use as therapeutically active sub stance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit RSV replication. For example, such amount may be below the amount that is toxic to normal cells, or the mammal as a whole.

In one example, the pharmaceutically effective amount of the compound of the invention administered parenterally per dose will be in the range of about 0.1 to about 50 mg/kg, alternatively about 0.1 to about 20 mg/kg of patient body weight per day, with the typical initial range of compound used being about 0.3 to about 15 mg/kg/day. In another embodiment, oral unit dosage forms, such as tablets and capsules, preferably contain from about 25 to about 100 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 mg to about 500 mg of the compound of the invention compounded with about 90 to about 30 mg anhydrous lactose, about 5 to about 40 mg sodium croscarmellose, about 5 to about 30 mg polyvinylpyrrolidone (PVP) K30, and about 1 to about 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 mg to 400 mg), of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

Indications and Methods of Treatment

The compounds of the invention can be utilized to inhibit RSV replication, therefore prevent synthesis of new viral RNA, protein, and infectious particles. Accordingly, the compounds of the invention are useful for the treatment or prophylaxis of RSV infection.

The invention relates to the use of a compound of formula I for the treatment or prophylaxis of respiratory syncytial virus infection.

The use of a compound of formula I for the preparation of medicaments useful in the treatment or prophylaxis diseases that are related to RSV infection is an object of the invention.

The invention relates in particular to the use of a compound of formula I for the preparation of a medicament for the treatment or prophylaxis of RSV infection.

Another embodiment includes a method of treating or preventing RSV infection in a mammal in need of such treatment, wherein the method comprises administering to said mammal a therapeutically effective amount of a compound of Formula I, a stereoisomer, tautomer, prodrug or pharmaceutically acceptable salt thereof.

Combination Therapy

The compounds of the invention can be used in combination with other antiviral ingredients for the treatment or prophylaxis of RSV infection.

EXAMPLES

The invention will be more fully understood by reference to the following examples. They should not, however, be construed as limiting the scope of the invention.

Abbreviations used herein are as follows:
μL: microliter
μm: micrometer
μM: micromoles per liter
MeOH-d$_4$: deuterated methanol
CDCl$_3$: deuterated chloroform
CDI: N, N-carbonyldiimidazole
DCC: dicyclohexylcarbodiimide
DCE: 1,2-dichloroethane
DMF: N',N-dimethylformamide
DMSO-d$_6$: deuterated dimethylsulfoxide
EtOH: ethanol
EC$_{50}$: the concentration of a compound where 50% of its maximal protection effect against viral induced CPE is observed
g: gram
HPLC: high performance liquid chromatography
Hz: Hertz
ICR: imprinting control region
J: coupling constants
LC/MS: Liquid chromatography/mass spectrometry
LongStrain: a subtype RSV strain obtained from ATCC with catalog number VR-26
mg: milligram
MHz: megahertz
mL: milliliter
mm: millimeter
mmol: millimole
MS (ESI): mass spectroscopy (electron spray ionization)
NBS: N-bromosuccinimide
NMP: N-methyl pyrrolidone
NMR: nuclear magnetic resonance
obsd.: observed
Prep HPLC: preparative high performance liquid chromatography
Rh$_2$Oct$_4$: rhodium octanoate dimer
THF: tetrahydrofuran
TLC: thin layer chromatography
δ: chemical shift
ppm: parts per million General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C$_{18}$ (5 OBD™ 30×100 mm) column or SunFire™ Perp C$_{18}$ (5 μm, OBD™ 30×100 mm) column.

LC/MS spectra were obtained using a MicroMass Plateform LC (Waters™ alliance 2795-ZQ2000). Standard LC/MS conditions were as follows (running time 6 minutes):

Acidic condition: A: 0.1% formic acid in H$_2$O; B: 0.1% formic acid in acetonitrile;
Basic condition: A: 0.01% NH$_3$.H$_2$O in H$_2$O; B: acetonitrile;
Neutral condition: A: H$_2$O; B: acetonitrile.

Mass spectra (MS): generally only ions which indicate the parent mass are reported, and unless otherwise stated the mass ion quoted is the positive mass ion (M+H)$^+$.

The microwave assisted reactions were carried out in a Biotage Initiator Sixty.

NMR Spectra were obtained using Bruker Avance 400 MHz.

All reactions involving air-sensitive reagents were performed under an argon atmosphere. Reagents were used as received from commercial suppliers without further purification unless otherwise noted.

The following examples were prepared by the general methods outlined in the schemes above. They are intended to illustrate the meaning of the present invention but should by no means represent a limitation within the meaning of the present invention.

Preparative Examples

Synthesis of Intermediates

Ethyl (Z)-3-(2-bromoanilino)-2-nitro-prop-2-enoate

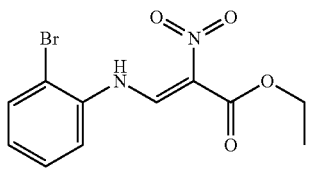 [SMILES: CCOC(=O)/C(=C/Nc1ccccc1Br)[N+](=O)[O-]]

To a mixture of 2-bromoaniline (6.46 g, 37.6 mmol) and ethyl 2-nitroacetate (5.0 g, 37.6 mmol) in ethanol (100 mL) was added acetic acid (5 mL). The mixture was stirred with refluxing for 30 minutes. Then triethoxymethane (11.0 g, 75.2 mmol) was added and the mixture was stirred under refluxing for 4 hours. After the mixture was cooled down, it was stood for 16 hours, and then it was filtrated to afford 4.0 g of ethyl 3-((2-bromophenyl)amino)-2-nitroacrylate as a yellow solid.

Ethyl 1-(2-bromophenyl)-2-methyl-1H-imidazole-4-carboxylate

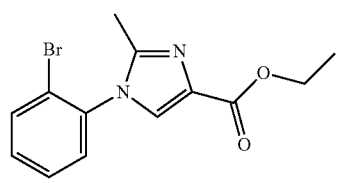 [SMILES: CCOC(=O)c1cn(-c2ccccc2Br)c(C)n1]

To a mixture of ethyl 3-((2-bromophenyl)amino)-2-nitroacrylate (2.0 g, 6.34 mmol) and 1,1,1-triethoxyethane (30 mL) in acetic acid (30 mL) was added ferric powder (1.8 g, 31.7 mmol) at room temperature. The mixture was stirred with refluxing for 2 hours, and then another piece of ferric powder (1.8 g, 31.7 mmol) was added in three portions during 5 hours. After the mixture was cooled down, it was filtered, and then the filtrate was concentrated in vacuo. The residue was purified by column chromatography (eluting with 75% ethyl acetate in petrol ether) to afford 0.5 g of ethyl 1-(2-bromophenyl)-2-methyl-1H-imidazole-4-carboxylate as a yellow powder.

1-(2-Bromophenyl)-2-methyl-1H-imidazole-4-carboxylic acid

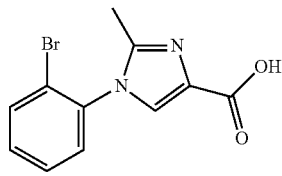 [SMILES: Cc1nc(C(=O)O)cn1-c1ccccc1Br]

To a mixture of ethyl 1-(2-bromophenyl)-2-methyl-1H-imidazole-4-carboxylate (0.5 g, 1.6 mmol) in EtOH (10 mL) was added 6 mL of NaOH solution (5N, aqueous). The mixture was stirred at room temperature for 5 hours. And then it was acidified with 5N HCl. The mixture was concentrated in vacuo and the residue was dispensed in a solution (10% methanol in dichloromethane, 20 mL). The mixture was stirred at room temperature for 1 hour. The mixture was filtered and the filtrate was concentrated to afford 0.35 g of 1-(2-bromophenyl)-2-methyl-1H-imidazole-4-carboxylic acid as a white powder.

N-Hydroxy-3,4,5-trimethoxybenzimidamide

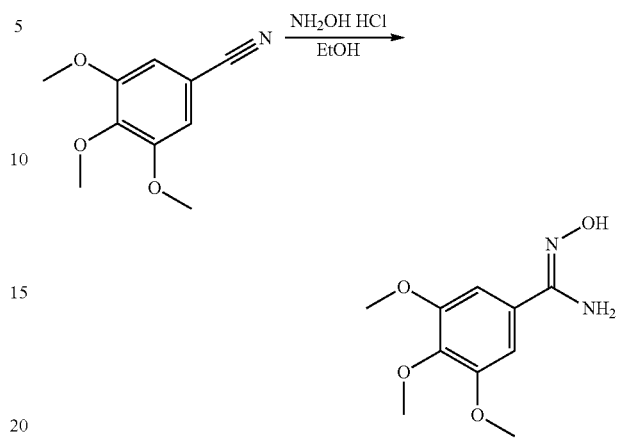

The mixture of 3,4,5-trimethoxybenzonitrile (15.0 g, 77.7 mmol) and aqueous hydroxylamine solution (22.8 mL, 50% in H$_2$O) in EtOH (150 mL) was stirred at 74° C. for 5 hours. After the mixture was cooled down, it was stood at room temperature for 10 hours. And then it was filtrated and 9.0 g of N-hydroxy-3,4,5-trimethoxybenzimidamide was afforded as a white powder.

Ethyl 3-ethoxy-2-nitrobut-2-enoate

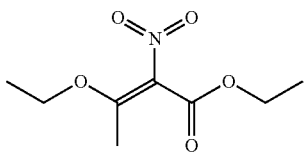

A mixture of ethyl 2-nitroacetate (5.0 g, 37.6 mmol) and 1,1,1-triethoxyethane (50 mL) was refluxed for 5 hours. And then it was concentrated in vacuo. The residue was used into the next step without further purification.

Ethyl 3-((2-bromophenyl)amino)-2-nitrobut-2-enoate

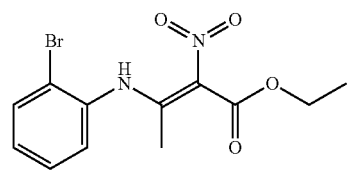 [SMILES: CCOC(=O)/C(=C(\C)Nc1ccccc1Br)[N+](=O)[O-]]

A mixture of ethyl 3-ethoxy-2-nitrobut-2-enoate (10 g, 49 mmol) and 2-bromoaniline (8.4 g, 49 mmol) in ethanol (200 mL) was stirred at room temperature for 16 hours. And then it was concentrated in vacuo, and the residue was purified by column chromatography (eluting with 6% acetone in petrol ether) to afford 2.8 g ethyl 3-((2-bromophenyl)amino)-2-nitrobut-2-enoate as a yellow solid.

Ethyl 1-(2-bromophenyl)-5-methyl-1H-imidazole-4-carboxylate

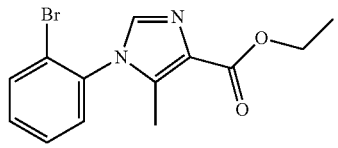 [SMILES: CCOC(=O)c1ncn(-c2ccccc2Br)c1C]

To a mixture of ethyl 3-((2-bromophenyl)amino)-2-nitrobut-2-enoate (3.29 g, 10 mmol) and triethoxymethane (50 mL) in acetic acid (50 mL) was added ferric powder (3.0 g, 54 mmol) at room temperature. The mixture was refluxed for 2 hours, and then another piece of ferric powder (3.0 g, 54 mmol) was added in three portions during 5 hours. After the reaction was cooled down, it was filtered and the filtrate was concentrated. The residue was purified by column chromatography (eluting from 10% ethyl acetate in petrol ether to 100% ethyl acetate) to afford 1.1 g of ethyl 1-(2-bromophenyl)-5-methyl-1H-imidazole-4-carboxylate as a yellow solid.

1-(2-Bromophenyl)-5-methyl-1H-imidazole-4-carboxylic acid

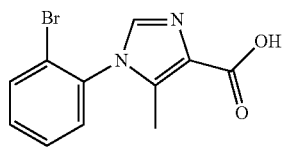 [SMILES: Cc1c(C(=O)O)ncn1-c1ccccc1Br]

To a mixture of ethyl 1-(2-bromophenyl)-5-methyl-1H-imidazole-4-carboxylate (3.0 g, 9.6 mmol) in EtOH (30 mL) was added 18 mL of NaOH solution (5N, aqueous). The mixture was stirred at room temperature for 5 hours. And then it was acidified with 5N HCl. The mixture was concentrated in vacuo and the residue was dissolved in a solution (10% methanol in dichloromethane, 50 mL). The mixture was stirred at room temperature for 1 hour. The mixture was filtered and the filtrate was concentrated to afford 2.0 g of 1-(2-bromophenyl)-5-methyl-1H-imidazole-4-carboxylic acid as a white powder.

Ethyl 1-(2-bromophenyl)-2,5-dimethyl-1H-imidazole-4-carboxylate

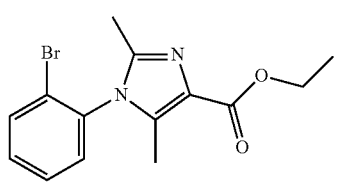 [SMILES: CCOC(=O)c1nc(C)n(-c2ccccc2Br)c1C]

To a mixture of ethyl 3-((2-bromophenyl)amino)-2-nitrobut-2-enoate (2.9 g, 8.8 mmol) and 1,1,1-triethoxyethane (45 mL) in acetic acid (45 mL) was added ferric powder (2.45 g, 44 mmol) at room temperature. The mixture was stirred with refluxing for 2 hours. And then another piece of ferric powder (2.45 g, 44 mmol) was added in three portions during 5 hours. After the mixture was cooled down, it was filtered and the filtrate was concentrated in vacuo. The residue was purified by column chromatography (eluting with 75% ethyl acetate in petrol ether) to afford 1.0 g of ethyl 1-(2-bromophenyl)-2,5-dimethyl-1H-imidazole-4-carboxylate as a yellow powder.

1-(2-bromophenyl)-2,5-dimethyl-1H-imidazole-4-carboxylic acid

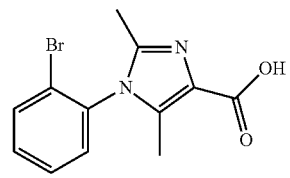 [SMILES: Cc1nc(C(=O)O)c(C)n1-c1ccccc1Br]

To a mixture of ethyl 1-(2-bromophenyl)-2,5-dimethyl-1H-imidazole-4-carboxylate (3.0 g, 9.3 mmol) in EtOH (30 mL) was added aqueous NaOH solution (15 ml, 5N). The mixture was stirred at room temperature for 5 hours. And then aqueous HCl solution (5N) was added to neutralize the mixture. The mixture was concentrated in vacuo. The residue was dissolved in 50 mL of 20% methanol in dichloromethane, and then stirred for 1 hour. The mixture was filtrated and the filtrate was concentrated to afford 2.0 g of 1-(2-bromophenyl)-2,5-dimethyl-1H-imidazole-4-carboxylic acid as a white powder.

(2-Chloropheny)-urea

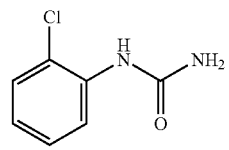 [SMILES: NC(=O)Nc1ccccc1Cl]

A suspension of sodium cyanate (5.1 g, 78 mmol) in $H_2O$ (100 mL) was added dropwise to a mixture of 2-chlorophenylamine (5.0 g, 39 mmol) in HOAc (5.6 mL) and $H_2O$ (7.8 mL) at room temperature. The mixture was stirred at room temperature for 6 hour and then filtered. The solid was dried under vacuum to afford 6.1 g of (2-chloro-pheny)-urea as a brown solid. LC/MS (m/z): 171 (M+1).

1-(2-Chloro-phenyl)-5-methyl-2-oxo-2,3-dihydro-1H-imidazole-4-carboxylic acid ethyl ester

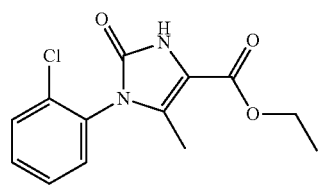 [SMILES: CCOC(=O)c1[nH]c(=O)n(-c2ccccc2Cl)c1C]

A suspension of $Rh_2Oct_4$ (200 mg) in toluene (10 mL) was added dropwise to a mixture of (2-chloro-pheny)-urea (3.3 g, 19.2 mmol) and ethyl diazoacetoacetate (2.0 g, 12.8 mmol) in DCE/toluene (40 mL/40 mL) at 80° C. The mixture was stirred at 80° C. for 1 hour and then cooled to room temperature. Trifluoroacetic acid (20 mL) was added and then the mixture was stirred at room temperature for 2 hours. The mixture was concentrated and then purified by column chromatography to give 2.4 g of 1-(2-chloro-phenyl)-5-methyl-2-oxo-2,3-dihydro-1H-imidazole-4-carboxylic acid ethyl ester as a brown solid. LC/MS (m/z): 281 (M+1).

2-Bromo-1-(2-chloro-phenyl)-5-methyl-1H-imidazole-4-carboxylic acid ethyl ester

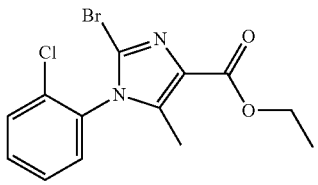 [SMILES: CCOC(=O)c1nc(Br)n(-c2ccccc2Cl)c1C]

A mixture of 1-(2-chloro-phenyl)-5-methyl-2-oxo-2,3-dihydro-1H-imidazole-4-carboxylic acid ethyl ester (1.0 g, 3.6 mmol) and phosphorus oxybromide (10.2 g, 35.6 mmol) in toluene (8 mL) was stirred at 100° C. for 14 hours. After the mixture was cooled to room temperature, saturated sodium bicarbonate solution was added to the mixture to adjust pH to 7. The mixture was extracted with ethyl acetate. The organic phase was dried over anhydrous Na$_2$SO$_4$ and then concentrated in vacuo. The residue was purified by column chromatography to afford 370 mg of 2-bromo-1-(2-chloro-phenyl)-5-methyl-1H-imidazole-4-carboxylic acid ethyl ester as a slight brown solid. LC/MS (m/z): 344 (M+1).

2-Bromo-1-(2-chloro-phenyl)-5-methyl-1H-imidazole-4-carboxylic acid

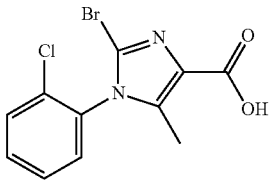 [SMILES: Cc1c(C(=O)O)nc(Br)n1-c1ccccc1Cl]

A mixture of 2-bromo-1-(2-chloro-phenyl)-5-methyl-1H-imidazole-4-carboxylic acid ethyl ester (370 mg, 1.1 mmol) and LiOH (226 mg, 5.4 mmol) in THF/H$_2$O (5 mL/5 mL) was stirred at 70° C. for 1 hour. HCl (aq, 1 M) was added to the mixture to adjust pH to 2. The mixture was extracted with ethyl acetate. The organic phase was dried over anhydrous Na$_2$SO$_4$ and then concentrated in vacuo to afford 340 mg of 2-bromo-1-(2-chloro-phenyl)-5-methyl-1H-imidazole-4-carboxylic acid as a slight brown solid. LC/MS (m/z): 316 (M+1).

Methyl 4-[(Z)—N'-hydroxycarbamimidoyl]-2-methyl-benzoate

Step 1: Synthesis of methyl 4-bromo-2-methyl-benzoate

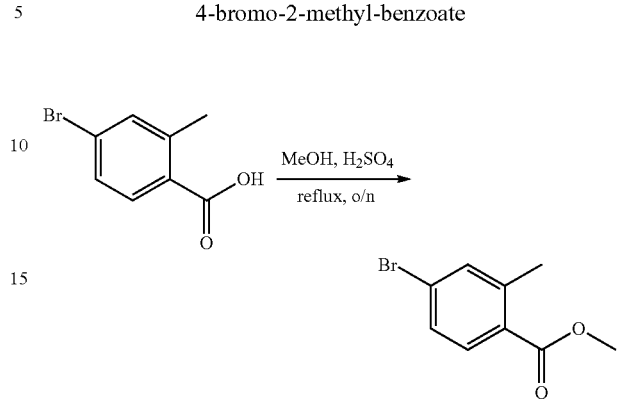

To a stirred solution of 4-bromo-2-methyl-benzoic acid (15 g, 65 mmol) in methanol (50 mL) was added sulfuric acid (2 mL). The mixture was stirred and refluxed for 15 hours. After the completion of the reaction, the mixture was quenched by water (20 mL) and then basified to pH 8. After most of the methanol was evaporated, the mixture was extracted with ethyl acetate (50 mL×3). The organic layer was washed by brine (20 mL), and then dried over sodium sulfate and then concentrated to give 15.3 g of methyl 4-bromo-2-methyl-benzoate as a white solid.

Step 2: Synthesis of methyl 4-cyano-2-methyl-benzoate

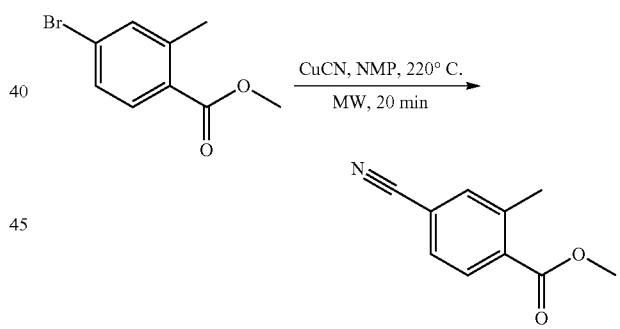

To a solution of methyl 4-bromo-2-methyl-benzoate (2.5 g, 11.0 mmol) in NMP (12 mL) was added cyanocopper (1.95 g, 22.0 mmol) in a sealed vial, the sealed vial was irradiated in the microwave on a Biotage Smith Synthesizer at 220° C. for 20 minutes. After the reaction was completed, the mixture was cooled to 0° C., and then 20 mL of ammonia was added dropwise. The mixture was stirred for 30 minutes at 0° C. and then was quenched by water/ethyl acetate (100 mL, 1/1). The mixture was filtered through a celite pad. The filtrate was partitioned between water/ethyl acetate. The aqueous layer was extracted with ethyl acetate (50 mL×3). The organic layer was washed with brine (30 mL), and then dried over sodium sulfate and evaporated to dryness. The residue was purified by column chromatography eluting with a gradient from 0% to 10% ethyl acetate in petroleum ether to give 0.9 g of methyl 4-cyano-2-methyl-benzoate as a white solid.

Step 3: Synthesis of methyl 4-[(Z)—N'-hydroxycarbamimidoyl]-2-methyl-benzoate

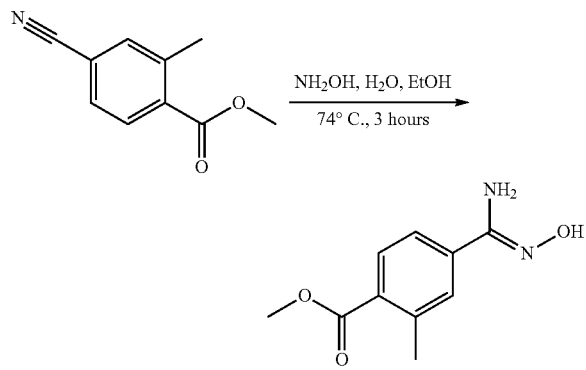

To a solution of methyl 4-cyano-2-methyl-benzoate (1.8 g, 10.3 mmol) in ethanol/water (30 mL, 2/1) was added hydrocholoride hydroxylamine (2.1 g, 31 mmol) and sodium carbonate (3.3 g, 31 mmol), the mixture was heated at 74° C. for 3 hours. After the completion of the reaction, the solution was evaporated. The residue was washed by water (20 mL) and then the mixture was filtered through a celite pad, the solid was collected to give 0.73 g of methyl 4-[(Z)—N'-hydroxycarbamimidoyl]-2-methyl-benzoate as a white solid.

Example 1-1

5-(1-(2-bromophenyl)-2-methyl-1H-imidazol-4-yl)-3-(3,4,5-trimethoxyphenyl)-1,2,4-oxadiazole To a mixture of 1-(2-bromophenyl)-2-methyl-1H-imidazole-4-carboxylic acid (140 mg, 0.5 mmol) and N'-hydroxy-3,4,5-trimethoxybenzimidamide (113 mg, 0.5 mmol) in anhydrous dioxane (5 mL) was added carbonyldiimidazole (206 mg, 1 mmol). The mixture was stirred at room temperature for 2 hours and then at 105° C. for 16 hours. The reaction mixture was concentrated in vacuo and the residue was purified by preparative HPLC to afford 50 mg of 5-(1-(2-bromophenyl)-2-methyl-1H-imidazol-4-yl)-3-(3,4,5-trimethoxyphenyl)-1,2,4-oxadiazole as white powder.

Example 1-2

5-[1-(2-Bromo-phenyl)-5-methyl-1H-imidazol-4-yl]-3-(3,4,5-trimethoxy-phenyl)-[1,2,4]oxadiazole The title compound was prepared in analogy to Example 1-1 by using 1-(2-bromophenyl)-5-methyl-1H-imidazole-4-carboxylic acid instead of 1-(2-bromophenyl)-2-methyl-1H-imidazole-4-carboxylic acid.

Example 1-3

5-(1-(2-bromophenyl)-2,5-dimethyl-1H-imidazol-4-yl)-3-(3,4,5-trimethoxyphenyl)-1,2,4-oxadiazole The title compound was prepared in analogy to Example 1-1 by using 1-(2-bromophenyl)-2,5-dimethyl-1H-imidazole-4-carboxylic acid instead of 1-(2-bromophenyl)-2-methyl-1H-imidazole-4-carboxylic acid.

Example 1-4

4-{5-[1-(2-Chloro-phenyl)-2,5-dimethyl-1H-imidazol-4-yl]-[1,2,4]oxadiazol-3-yl}-benzoic acid methyl ester The title compound was prepared in analogy to Example 1-1 by using 1-(2-chloro-phenyl)-2,5-dimethyl-1H-imidazole-4-carboxylic acid and 4-(N-hydroxycarbamimidoyl)-benzoic acid methyl ester instead of 1-(2-bromophenyl)-2-methyl-1H-imidazole-4-carboxylic acid and N-hydroxy-3,4,5-trimethoxybenzimidamide.

Example 1-5

5-[1-(2-Chlorophenyl)-2,5-dimethyl-1H-imidazol-4-yl]-3-(4-methoxy-phenyl)-[1,2,4]oxadiazole The title compound was prepared in analogy to Example 1-1 by using 1-(2-bromophenyl)-2,5-dimethyl-1H-imidazole-4-carboxylic acid and 4-N'-hydroxy-4-methoxy-benzamidine instead of 1-(2-bromophenyl)-2-methyl-1H-imidazole-4-carboxylic acid and N'-hydroxy-3,4,5-trimethoxybenzimidamide.

Example 1-6

5-(1-(2,6-dimethylphenyl)-5-methyl-1H-imidazol-4-yl)-3-(3,4,5-trimethoxyphenyl)-1,2,4-oxadiazole The title compound was prepared in analogy to Example 1-1 by using 1-(2,6-dimethylphenyl)-5-methyl-1H-imidazole-4-carboxylic acid instead of 1-(2-bromophenyl)-2-methyl-1H-imidazole-4-carboxylic acid.

Example 1-7

5-[1-(2-bromo-phenyl)-2,5-dimethyl-1H-imidazol-4-yl]-3-(2,5-dimethoxy-phenyl)-[1,2,4]oxadiazole The title compound was prepared in analogy to Example 1-1 by using 1-(2-bromophenyl)-2,5-dimethyl-1H-imidazole-4-carboxylic acid and N-hydroxy-2,5-dimethoxy-benzamidine instead of 1-(2-bromophenyl)-2-methyl-1H-imidazole-4-carboxylic acid and N'-hydroxy-3,4,5-trimethoxybenzimidamide.

Example 1-8

5-[1-(2-chloro-6-methyl-phenyl)-5-dimethyl-1H-imidazol-4-yl]-3-(2,4-dimethoxy-phenyl)-[1,2,4]oxadiazole The title compound was prepared in analogy to Example 1-1 by using 1-(2-chloro-6-methylphenyl)-5-methyl-1H-imidazole-4-carboxylic acid and N-hydroxy-2,4-dimethoxy-benzamidine instead of 1-(2-bromophenyl)-2-methyl-1H-imidazole-4-carboxylic acid and N'-hydroxy-3,4,5-trimethoxybenzimidamide.

Example 1-9

5-[1-(2-chloro-6-methyl-phenyl)-5-methyl-imidazol-4-yl]-3-(3,4,5-trimethoxyphenyl)-1,2,4-oxadiazole The title compound was prepared in analogy to Example 1-1 by using 1-(2-chloro-6-methylphenyl)-5-methyl-1H- imidazole-4-carboxylic acid and N-hydroxy-3,4,5-trimethoxy-benzamidine instead of 1-(2-bromophenyl)-2-methyl-1H-imidazole-4-carboxylic acid and N'-hydroxy-3,4,5-trimethoxybenzimidamide.

Example 1-10

5-(1-(2,6-dimethylphenyl)-5-methyl-1H-imidazol-4-yl)-3-(4-methoxyphenyl)-1,2,4-oxadiazol The title compound was prepared in analogy to Example 1-1 by using 1-(2,6-dimethylphenyl)-5-dimethyl-1H-imidazole-4-carboxylic acid and N-hydroxy-4-methoxy-benzamidine instead of 1-(2-bromophenyl)-2-methyl-1H-imidazole-4-carboxylic acid and N'-hydroxy-3,4,5-trimethoxybenzimidamide.

Example 1-11

5-[1-(2-Chloro-phenyl)-2,5-dimethyl-1H-imidazol-4-yl]-3-(4-methoxy-phenyl)-[1,2,4]oxadiazole The title compound was prepared in analogy to Example 1-1 by using 1-(2-chlorophenyl)-2,5-dimethyl-1H-imidazole-4-carboxylic acid and N-hydroxy-4-methoxy-benzamidine instead of 1-(2-bromophenyl)-2-methyl-1H-imidazole-4-carboxylic acid and N'-hydroxy-3,4,5-trimethoxybenzimidamide.

Example 1-12

3-(2,4-Dimethoxy-phenyl)-5-[1-(2,6-dimethyl-phenyl)-5-methyl-1H-imidazol-4-yl]-[1,2,4]oxadiazole The title compound was prepared in analogy to Example 1-1 by using 1-(2,6-dimethylphenyl)-5-methyl-1H-imidazole-4-carboxylic acid and N-hydroxy-2,5-dimethoxy-benzamidine instead of 1-(2-bromophenyl)-2-methyl-1H-imidazole-4-carboxylic acid and N'-hydroxy-3,4,5-trimethoxybenzimidamide.

Example 1-13

4-{5-[1-(2-Chloro-phenyl)-2,5-dimethyl-1H-imidazol-4-yl]-[1,2,4]oxadiazol-3-yl}-2-methoxy-benzoic acid methyl ester The title compound was prepared in analogy to Example 1-1 by using 1-(2-chlorophenyl)-2,5-dimethyl-1H-imidazole-4-carboxylic acid and methyl 4-[N'-hydroxycarbamimidoyl]-2-methoxy benzoate instead of 1-(2-bromophenyl)-2-methyl-1H-imidazole-4-carboxylic acid and N'-hydroxy-3,4,5-trimethoxybenzimidamide.

Example 1-14

5-[1-(2-Chloro-phenyl)-2,5-dimethyl-1H-imidazol-4-yl]-3-(2-methoxy-phenyl)-[1,2,4]oxadiazole The title compound was prepared in analogy to Example 1-1 by using 1-(2-chlorophenyl)-2,5-dimethyl-1H-imidazole-4-carboxylic acid and N-hydroxy-2-dimethoxy-benzamidine instead of 1-(2-bromophenyl)-2-methyl-1H-imidazole-4-carboxylic acid and N'-hydroxy-3,4,5-trimethoxybenzimidamide.

Example 1-15

5-[1-(2-Chloro-6-methyl-phenyl)-5-methyl-1H-imidazol-4-yl]-3-(4-methoxy-phenyl)-[1,2,4]oxadiazole The title compound was prepared in analogy to Example 1-1 by using 1-(2-chloro-6-methylphenyl)-5-methyl-1H-imidazole-4-carboxylic acid and N-hydroxy-4-methoxyl-benzamidine instead of 1-(2-bromophenyl)-2-methyl-1H-imidazole-4-carboxylic acid and N'-hydroxy-3,4,5-trimethoxybenzimidamide.

Example 1-16

5-[1-(2-Chloro-phenyl)-2,5-dimethyl-1H-imidazol-4-yl]-3-(2,4-dimethoxy-phenyl)-[1,2,4]oxadiazole The title compound was prepared in analogy to Example 1-1 by using 1-(2-chloro-phenyl)-2,5-dimethyl-1H-imidazole-4-carboxylic acid and N-hydroxy-2,4-dimethoxy-benzamidine instead of 1-(2-bromophenyl)-2-methyl-1H-imidazole-4-carboxylic acid and N'-hydroxy-3,4,5-trimethoxybenzimidamide.

Example 1-17

5-(1-(2-Bromophenyl)-2-methyl-1H-imidazol-4-yl)-3-(3,4,5-trimethoxyphenyl)-1,2,4-oxadiazole The title compound was prepared in analogy to Example 1-1 by using 1-(2-chlorophenyl)-2,5-dimethyl-1H-imidazole-4-carboxylic acid and N-hydroxy-2,5-dimethoxylbenzamidine instead of 1-(2-bromophenyl)-2-methyl-1H-imidazole-4-carboxylic acid and N'-hydroxy-3,4,5-trimethoxybenzimidamide.

Example 1-18

5-[1-(2-Chloro-phenyl)-2,5-dimethyl-1H-imidazol-4-yl]-3-(3,4,5-trimethoxy-phenyl)-[1,2,4]oxadiazole The title compound was prepared in analogy to Example 1-1 by using 1-(2-chlorophenyl)-2,5-dimethyl-1H-imidazole-4-carboxylic acid and N-hydroxy-3,4,5-trimethoxyl-benzamidine instead of 1-(2-bromophenyl)-2-methyl-1H-imidazole-4-carboxylic acid and N'-hydroxy-3,4,5-trimethoxybenzimidamide.

Example 1-19

4-{5-[1-(2-Chloro-phenyl)-2,5-dimethyl-1H-imidazol-4-yl]-[1,2,4]oxadiazol-3-yl}-3-methoxy-benzoic acid methyl ester The title compound was prepared in analogy to Example 1-1 by using 1-(2-chlorophenyl)-2,5-dimethyl-1H-imidazole-4-carboxylic acid and methyl 4[N'-hydroxycarbamimidoyl]-2-methoxylbenzoate instead of 1-(2-bromophenyl)-2-methyl-1H-imidazole-4-carboxylic acid and N'-hydroxy-3,4,5-trimethoxybenzimidamide.

Example 1-20

5-[1-(2-Chloro-phenyl)-2,5-dimethyl-1H-imidazol-4-yl]-3-(2-fluoro-4-methoxy-phenyl)-[1,2,4]oxadiazole The title compound was prepared in analogy to Example 1-1 by using 1-(2-chlorophenyl)-2,5-dimethyl-1H-imidazole-4-carboxylic acid and N-hydroxy-2-floro-4-methoxy-benzamidine instead of 1-(2-bromophenyl)-2-methyl-1H-imidazole-4-carboxylic acid and N'-hydroxy-3,4,5-trimethoxybenzimidamide.

Example 1-21

4-{5-[1-(2-Chloro-phenyl)-2,5-dimethyl-1H-imidazol-4-yl]-[1,2,4]oxadiazol-3-yl}-2-methyl-benzoic acid methyl ester The title compound was prepared in analogy to Example 1-1 by using 1-(2-chlorophenyl)-2,5-dimethyl-1H-imidazole-4-carboxylic acid and methyl 4-[N'-hydroxycarbamimidoyl]-2-methyl benzoate instead of 1-(2-bromophenyl)-2-methyl-1H-imidazole-4-carboxylic acid and N'-hydroxy-3,4,5-trimethoxybenzimidamide.

Example 1-22

5-[1-(2-Chloro-phenyl)-2,5-dimethyl-1H-imidazol-4-yl]-3-(3-methoxy-phenyl)-[1,2,4]oxadiazole The title compound was prepared in analogy to Example 1-1 by using 1-(2-chlorophenyl)-2,5-dimethyl-1H-imidazole-4-carboxylic acid and N-hydroxy-3-methoxy-benzamidine instead of 1-(2-bromophenyl)-2-methyl-1H-imidazole-4-carboxylic acid and N'-hydroxy-3,4,5-trimethoxybenzimidamide.

Example 1-23

5-[1-(2-Methoxy-phenyl)-2,5-dimethyl-1H-imidazol-4-yl]-3-(3,4,5-trimethoxy-phenyl)-[1,2,4]oxadiazole The title compound was prepared in analogy to Example 1-1 by using 1-(2-methoxyphenyl)-2,5-dimethyl-1H-imidazole-4-carboxylic acid and N-hydroxy-3,4,5-trimethoxy-benzamidine instead of 1-(2-bromophenyl)-2-methyl-1H-imidazole-4-carboxylic acid and N'-hydroxy-3,4,5-trimethoxybenzimidamide.

Example 1-24

5-[2-Bromo-1-(2-chloro-phenyl)-5-methyl-1H-imidazol-4-yl]-3-(3,4,5-trimethoxy-phenyl)-[1,2,4]oxadiazole The title compound was prepared in analogy to Example 1-1 by using 1-(2-chloroyphenyl)-2-bromo-1H-imidazole-4-carboxylic acid and N-hydroxy-3,4,5-trimethoxy-benzamidine instead of 1-(2-bromophenyl)-2-methyl-1H-imidazole-4-carboxylic acid and N'-hydroxy-3,4,5-trimethoxybenzimidamide.

Example 1-25

5-[5-(2-Chlorophenyl)-1-methyl-imidazol-2-yl]-3-(3,4,5-trimethoxyphenyl)-1,2,4-oxadiazole The title compound was prepared in analogy to Example 1-1 by using 5-(2-chlorophenyl)-1-methyl-imidazole-2-carboxylic acid and N-hydroxy-3,4,5-trimethoxy-benzamidine instead of 1-(2-bromophenyl)-2-methyl-1H-imidazole-4-carboxylic acid and N'-hydroxy-3,4,5-trimethoxybenzimidamide.

Example 1-26

5-[2-(2-Chlorophenyl)-3-methyl-imidazol-4-yl]-3-(3,4,5-trimethoxyphenyl)-1,2,4-oxadiazole The title compound was prepared in analogy to Example 1-1 by using 2-(2-chlorophenyl)-3-methyl-imidazole-4-carboxylic acid and N-hydroxy-3,4,5-trimethoxy-benzamidine instead of 1-(2-bromophenyl)-2-methyl-1H-imidazole-4-carboxylic acid and N'-hydroxy-3,4,5-trimethoxybenzimidamide.

Example 2-1

4-[5-[1-(2-Chloro-6-methyl-phenyl)-5-methyl-imidazol-4-yl]-1,2,4-oxadiazol-3-yl]-3-methoxy-benzoic acid Step 1. Synthesis of methyl 4-[5-[1-(2-chloro-6-methyl-phenyl)-5-methyl-imidazol-4-yl]-1,2,4-oxadiazol-3-yl]-3-methoxy-benzoate

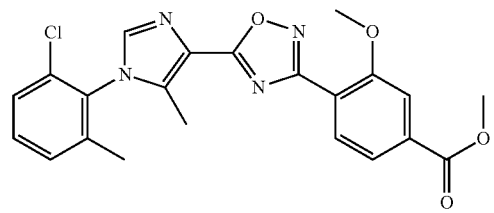 [SMILES: COC(=O)c1ccc(-c2noc(-c3ncn(-c4c(C)cccc4Cl)c3C)n2)c(OC)c1]

Methyl 4-[5-[1-(2-chloro-6-methyl-phenyl)-5-methyl-imidazol-4-yl]-1,2,4-oxadiazol-3-yl]-3-methoxy-benzoate was prepared in analogy to Example 1-1 by using 1-(2-chloro-6-methylphenyl)-5-dimethyl-1H-imidazole-4-carboxylic acid and methyl 4-[N'-hydroxycarbamimidoyl]-3-methoxylbenzoate instead of 1-(2-bromophenyl)-2-methyl-1H-imidazole-4-carboxylic acid and N'-hydroxy-3,4,5-trimethoxybenzimidamide.

Step 2. Synthesis of 4-[5-[1-(2-chloro-6-methyl-phenyl)-5-methyl-imidazol-4-yl]-1,2,4-oxadiazol-3-yl]-3-methoxy-benzoic acid To a solution of mixture of methyl 4-[5-[1-(2-chloro-6-methylphenyl)-5-methyl-imidazol-4-yl]-1,2,4-oxadiazol-3-yl]-3-methoxy-benzoate (55 mg, 0.13 mmol) in tetrahydrofuran (5 mL) was added lithium hydroxide (31 mg, 1.3 mmol) in water (1 mL). The mixture was stirred at 20° C. for 15 hours. After the completion of the reaction, the solution was adjusted to pH 3 with 2 M HCl, and then tetrahydrofuran was evaporated. The mixture was filtered through a celite pad, and the solid was collected as a white solid.

Example 2-2

4-{5-[1-(2-Chloro-phenyl)-2,5-dimethyl-1H-imidazol-4-yl]-[1,2,4]oxadiazol-3-yl}-benzoic acid The title compound was prepared in analogy to Example 2-1 by using 4-{5-[1-(2-chloro-phenyl)-2,5-dimethyl-1H-imidazol-4-yl]-[1,2,4]oxadiazol-3-yl}-benzoic acid methyl ester instead of methyl 4-[5-[1-(2-chloro-6-methylphenyl)-5-methyl-imidazol-4-yl]-1,2,4-oxadiazol-3-yl]-3-methoxy-benzoate.

Example 2-3

4-{5-[1-(2,6-Dimethyl-phenyl)-5-methyl-1H-imidazol-4-yl]-[1,2,4]oxadiazol-3-yl}-3-methoxy-benzoic acid The title compound was prepared in analogy to Example 2-1 by using 4-{5-[1-(2,6-dimethylphenyl)-5-methyl-1H-imidazol-4-yl]-[1,2,4]oxadiazol-3-yl}-2-methoxy-benzoic acid methyl ester instead of methyl 4-[5-[1-(2-chloro-6-methylphenyl)-5-methyl-imidazol-4-yl]-1,2,4-oxadiazol-3-yl]-3-methoxy-benzoate.

Example 2-4

4-{5-[1-(2,6-Dimethyl-phenyl)-5-methyl-1H-imidazol-4-yl]-[1,2,4]oxadiazol-3-yl}-2-methoxy-benzoic acid The title compound was prepared in analogy to Example 2-1 by using 4-{5-[1-(2,6-dimethylphenyl)-5-dimethyl-1H-imidazol-4-yl]-[1,2,4]oxadiazol-3-yl}-3-methoxy-benzoic acid methyl ester instead of methyl 4-[5-[1-(2-chloro-6-methylphenyl)-5-methyl-imidazol-4-yl]-1,2,4-oxadiazol-3-yl]-3-methoxy-benzoate.

Example 2-5

4-{5-[1-(2-Chloro-6-methyl-phenyl)-5-methyl-1H-imidazol-4-yl]-[1,2,4]oxadiazol-3-yl}-2-methoxy-benzoic acid Step 1. Synthesis of methyl 4-[5-[1-(2-chloro-6-methyl-phenyl)-5-methyl-imidazol-4-yl]-1,2,4-oxadiazol-3-yl]-2-methoxy-benzoate

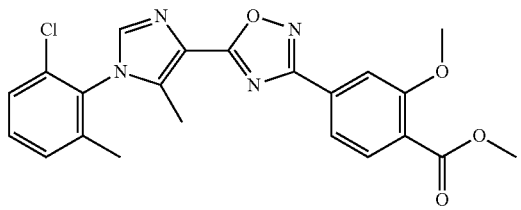 [SMILES: COC(=O)c1ccc(-c2noc(-c3ncn(-c4c(C)cccc4Cl)c3C)n2)cc1OC]

Methyl 4-[5-[1-(2-chloro-6-methyl-phenyl)-5-methyl-imidazol-4-yl]-1,2,4-oxadiazol-3-yl]-2-methoxy-benzoate was prepared in analogy to Example 1-1 by using 1-(2-chloro-6-methylphenyl)-5-methyl-1H-imidazole-4-carboxylic and methyl 4-[N'-hydroxycarbamimidoyl]-2-methoxyl-benzoate instead of 1-(2-bromophenyl)-2-methyl-1H-imidazole-4-carboxylic acid and N'-hydroxy-3,4,5-trimethoxybenzimidamide.

Step 2. Synthesis of 4-{5-[1-(2-chloro-6-methyl-phenyl)-5-methyl-1H-imidazol-4-yl]-[1,2,4]oxadiazol-3-yl}-2-methoxy-benzoic acid The title compound was prepared in analogy to Example 2-1 by using 4-{5-[1-(2-chloro-6-methylphenyl)-5-dimethyl-1H-imidazol-4-yl]-[1,2,4]oxadiazol-3-yl}-3-methoxy-benzoic acid methyl ester instead of methyl 4-[5-[1-(2-chloro-6-methylphenyl)-5-methyl-imidazol-4-yl]-1,2,4-oxadiazol-3-yl]-3-methoxy-benzoate.

Example 3-1

(1-(2-Chlorophenyl)-5-methyl-4-(3-(3,4,5-trimethoxyphenyl)-1,2,4-oxadiazol-5-yl)-1H-imidazol-2-yl)methanol Step 1: Synthesis of 5-(1-(2-chlorophenyl)-5-methyl-1H-imidazol-4-yl)-3-(3,4,5-trimethoxyphenyl)-1,2,4-oxadiazole

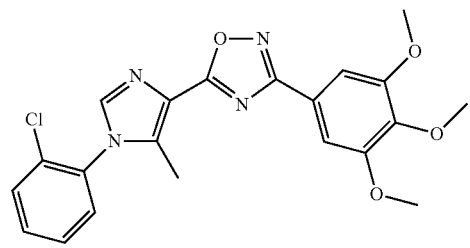 [SMILES: COc1cc(-c2noc(-c3ncn(-c4ccccc4Cl)c3C)n2)cc(OC)c1OC]

5-(1-(2-Chlorophenyl)-5-methyl-1H-imidazol-4-yl)-3-(3,4,5-trimethoxyphenyl)-1,2,4-oxadiazole was prepared in analogy to Example 1-1 by using 1-(2-chlorophenyl)-5-methyl-1H-imidazole-4-carboxylic instead of 1-(2-bromophenyl)-2-methyl-1H-imidazole-4-carboxylic acid.

Step 2: Synthesis of (1-(2-chlorophenyl)-5-methyl-4-(3-(3,4,5-trimethoxyphenyl)-1,2,4-oxadiazol-5-yl)-1H-imidazol-2-yl)methanol The mixture of 5-(1-(2-chlorophenyl)-5-methyl-1H-imidazol-4-yl)-3-(3,4,5-trimethoxyphenyl)-1,2,4-oxadiazole (0.43 g, 1 mmol) in DMSO (10 mL) was added paraformaldehyde (0.3 g, 10 mmol). The mixture was stirred at 130° C. in a sealed tube for 48 hours. The reaction mixture was dissolved in 100 mL of ethyl acetate, and then washed with $H_2O$ (20 mL×3) and brine, and then dried over $Na_2SO_4$ and concentrated. The residue was purified by column chromatography (eluting from 30% ethyl acetate in petrol ether to 100% ethyl acetate) to afford 90 mg of product as a white powder.

Example 3-2

1-(2-Chlorophenyl)-5-methyl-4-(3-(3,4,5-trimethoxyphenyl)-1,2,4-oxadiazol-5-yl)-1H-imidazole-2-carboxylic acid Step 1. Synthesis of 1-(2-chlorophenyl)-5-methyl-4-(3-(3,4,5-trimethoxyphenyl)-1,2,4-oxadiazol-5-yl)-1H-imidazole-2-carbaldehyde

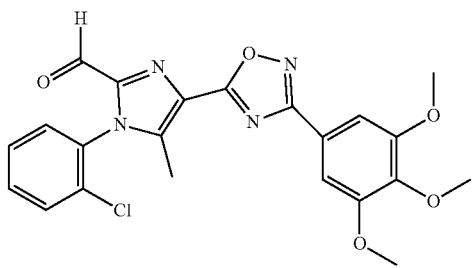 [SMILES: COc1cc(-c2noc(-c3nc(C=O)n(-c4ccccc4Cl)c3C)n2)cc(OC)c1OC]

To a mixture of (1-(2-chlorophenyl)-5-methyl-4-(3-(3,4,5-trimethoxyphenyl)-1,2,4-oxadiazol-5-yl)-1H-imidazol-2-yl)methanol (91 mg, 0.2 mmol, Example 2-1) in MeCN (10 mL) was added Dess Martin reagent (254 mg, 0.6 mmol) at 0° C. The mixture was stirred at room temperature and the reaction was monitored by TLC. After 30 minutes, saturated $Na_2S_2O_3$ solution (4 mL) was added and the mixture was stirred for another 5 minutes, followed by the addition of saturated $NaHCO_3$ solution (4 mL). Ethyl acetate (100 mL) was added and the mixture was washed with $H_2O$ (20 mL) and brine (20 mL), and then dried over $Na_2SO_4$ and then concentrated in vacuo. The residue was purified by column chromatography (eluting from 30% ethyl acetate in petrol ether to 60% ethyl acetate in petrol ether) to afford 90 mg of product as a white powder.

Step 2. Synthesis of 1-(2-chlorophenyl)-5-methyl-4-(3-(3,4,5-trimethoxyphenyl)-1,2,4-oxadiazol-5-yl)-1H-imidazole-2-carboxylic acid 1-(2-Chlorophenyl)-5-methyl-4-(3-(3,4,5-trimethoxyphenyl)-1,2,4-oxadiazol-5-yl)-1H-imidazole-2-carbaldehyde (90 mg, 0.2 mmol) in DMF (5 mL) was added $K_2PO_4$ solution (1 mL, 1M/L in water) and $KMnO_4$ (158 mg, 2 mmol). After the mixture was stirred at room temperature for 2 hours, another piece of $KMnO_4$ (158 mg, 1 mmol) was added and the mixture was stirred for another 2 hours. The reaction was monitored by TLC. After 1-(2-chlorophenyl)-5-methyl-4-(3-(3,4,5-trimethoxyphenyl)-1,2,4-oxadiazol-5-yl)-1H-imidazole-2-carbaldehyde was disappeared, $Na_2S_2O_3$ (0.5 g) was added and the mixture was stirred for 5 minutes. The mixture was filtrated and the filtrate was purified by preparative HPLC to afford 30 mg of title product as a white powder.

Biological Examples

Example 4

Viral Cytopathic Effect (CPE) Assay

To measure anti-RSV activity of compounds, 96-well plates were seeded with $6\times10^3$ cells per well in Dulbecco's modified Eagle's medium (DMEM) containing 10% fetal bovine serum (FBS). Cells were infected the next day with sufficient RSV Long strain (ATCC) to produce an approximately 80-90% cytopathic effect after 5 days, in the presence of serial half-log diluted compound in a total volume of 200 µL per well. The viability of cells is assessed after 5 days using Cell Counting kit-8 (Dojindo Molecular Technologies). The absorbance at 450 nm and referenced at 630 nm is measured to determine 50% effective concentration ($EC_{50}$).

The compounds of the present invention were tested for their anti-RSV activity, and the activation as described herein. The Examples were tested in the above assay and found to have $EC_{50}$ of about 0.001 µM to about 10 µM. Particular compound of formula (I) were found to have $EC_{50}$ of about 0.001 µM to about 1 µM. Further particular compound of formula (I) were found to have $EC_{50}$ of about 0.001 µM to about 0.1 µM.

Results of CPE assays are given in Table 1.

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. Compounds of formula (I)

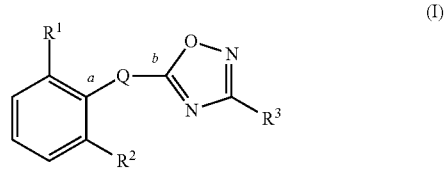

wherein
R$^1$ is hydrogen, C$_{1-6}$alkyl, C$_{1-6}$alkoxy or halogen;
R$^2$ is hydrogen, C$_{1-6}$alkyl or halogen;
provided that R$^1$ and R$^2$ are not hydrogen simultaneously;
R$^3$ is

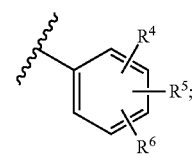

wherein R$^4$ is C$_{1-6}$alkoxy, C$_{1-6}$alkoxycarbonyl, carboxy or halogen;
R$^5$ is hydrogen, C$_{1-6}$alkyl or C$_{1-6}$alkoxy;
R$^6$ is hydrogen or C$_{1-6}$alkoxy;
Q is

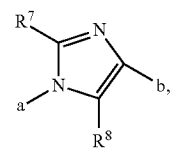

-continued

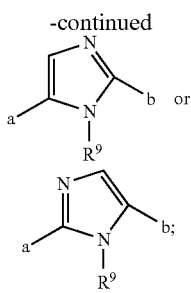

wherein R⁷ is hydrogen, $C_{1-6}$alkyl, carboxy, hydroxy-CH₂— or halogen;
R⁸ is hydrogen or $C_{1-6}$alkyl;
R⁹ is $C_{1-6}$alkyl;
or pharmaceutically acceptable salts thereof.

2. A compound according to claim 1, wherein
R¹ is hydrogen, methyl, methoxy, chloro or bromo;
R² is hydrogen, methyl or chloro;
provided that R¹ and R² are not hydrogen simultaneously;
R³ is

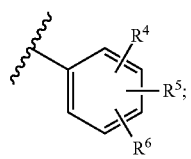

wherein R⁴ is methoxy, methoxycarbonyl, carboxy or fluoro;
R⁵ is hydrogen, methyl or methoxy;
R⁶ is hydrogen or methoxy;
Q is

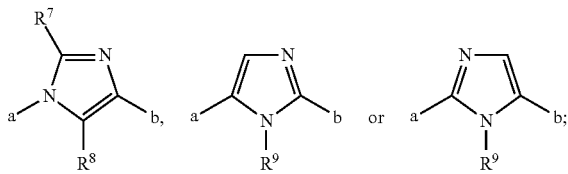

wherein R⁷ is hydrogen, methyl, carboxy, hydroxy-CH₂— or bromo;
R⁸ is hydrogen or methyl;
R⁹ is methyl;
or pharmaceutically acceptable salts thereof.

3. A compound according to claim 1 or a pharmaceutically acceptable salt thereof, wherein
R¹ is $C_{1-6}$alkyl or halogen;
R² is hydrogen or $C_{1-6}$alkyl;
R³ is

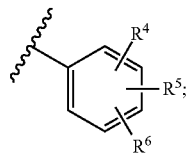

wherein R⁴ is $C_{1-6}$alkoxy or carboxy;
R⁵ is hydrogen or $C_{1-6}$alkoxy;
R⁶ is hydrogen or $C_{1-6}$alkoxy;
Q is

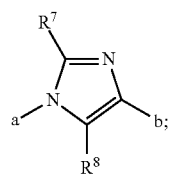

wherein one of R⁷ and R⁸ is $C_{1-6}$alkyl, and the other one is hydrogen.

4. A compound according to claim 1 or a pharmaceutically acceptable salt thereof, wherein
R¹ is methyl, chloro or bromo;
R² is hydrogen or methyl;
R³ is

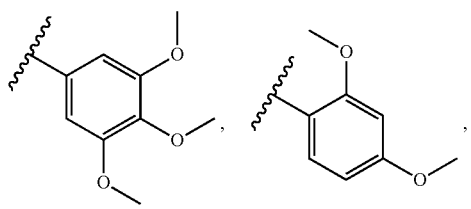

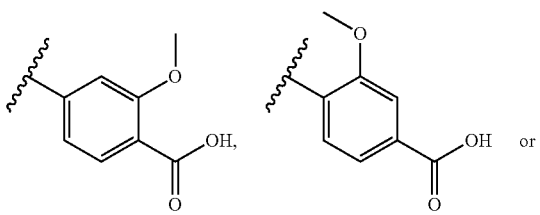

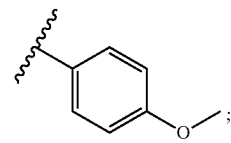

Q is

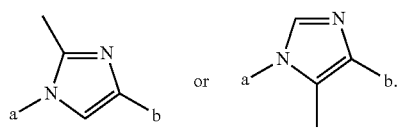

5. A compound according to claim 1 or a pharmaceutically acceptable salt thereof, wherein
R¹ is $C_{1-6}$alkoxy or halogen;
R² is hydrogen;

R³ is

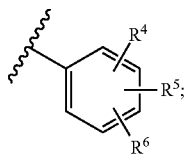

wherein R⁴ is $C_{1-6}$ alkoxy, $C_{1-6}$alkoxycarbonyl, carboxy or halogen;
R⁵ is hydrogen, $C_{1-6}$alkyl or $C_{1-6}$alkoxy;
R⁶ is hydrogen or $C_{1-6}$alkoxy;
Q is

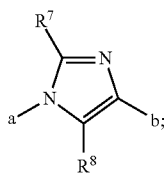

wherein R⁷ is $C_{1-6}$alkyl, hydroxy-CH₂— or halogen;
R⁸ is $C_{1-6}$alkyl.

6. A compound according to claim 1 or a pharmaceutically acceptable salt thereof, wherein
R¹ is methoxy, chloro or bromo;
R² is hydrogen;
R³ is

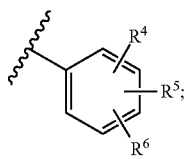

wherein R⁴ is methoxy, methoxycarbonyl, carboxy or fluoro;
R⁵ is hydrogen, methyl or methoxy;
R⁶ is hydrogen or methoxy;
Q is

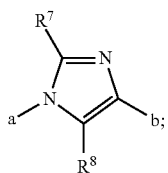

wherein R⁷ is methyl, hydroxy-CH₂— or bromo;
R⁸ is methyl.

7. A compound according to claim 1, selected from
5-(1-(2-Bromophenyl)-2-methyl-1H-imidazol-4-yl)-3-(3,4,5-trimethoxyphenyl)-1,2,4-oxadiazole;
5-[1-(2-Bromo-phenyl)-5-methyl-1H-imidazol-4-yl]-3-(3,4,5-trimethoxy-phenyl)-[1,2,4]oxadiazole;
5-(1-(2-Bromophenyl)-2,5-dimethyl-1H-imidazol-4-yl)-3-(3,4,5-trimethoxyphenyl)-1,2,4-oxadiazole;
4-{5-[1-(2-Chloro-phenyl)-2,5-dimethyl-1H-imidazol-4-yl]-[1,2,4]oxadiazol-3-yl}-benzoic acid methyl ester;
5-[1-(2-Chlorophenyl)-2,5-dimethyl-1H-imidazol-4-yl]-3-(4-methoxy-phenyl)-[1,2,4]oxadiazole;
5-(1-(2,6-Dimethylphenyl)-5-methyl-1H-imidazol-4-yl)-3-(3,4,5-trimethoxyphenyl)-1,2,4-oxadiazole;
5-[1-(2-Bromo-phenyl)-2,5-dimethyl-1H-imidazol-4-yl]-3-(2,5-dimethoxy-phenyl)-[1,2,4]oxadiazole;
5-[1-(2-Chloro-6-methyl-phenyl)-5-methyl-1H-imidazol-4-yl]-3-(2,4-dimethoxy-phenyl)-[1,2,4]oxadiazole;
5-[1-(2-Chloro-6-methyl-phenyl)-5-methyl-imidazol-4-yl]-3-(3,4,5-trimethoxyphenyl)-1,2,4-oxadiazole;
5-(1-(2,6-Dimethylphenyl)-5-methyl-1H-imidazol-4-yl)-3-(4-methoxyphenyl)-1,2,4-oxadiazol;
5-[1-(2-Chloro-phenyl)-2,5-dimethyl-1H-imidazol-4-yl]-3-(4-methoxy-phenyl)-[1,2,4]oxadiazole;
3-(2,4-Dimethoxy-phenyl)-5-[1-(2,6-dimethyl-phenyl)-5-methyl-1H-imidazol-4-yl]-[1,2,4]oxadiazole;
4-{5-[1-(2-Chloro-phenyl)-2,5-dimethyl-1H-imidazol-4-yl]-[1,2,4]oxadiazol-3-yl}-2-methoxy-benzoic acid methyl ester;
5-[1-(2-Chloro-phenyl)-2,5-dimethyl-1H-imidazol-4-yl]-3-(2-methoxy-phenyl)-[1,2,4]oxadiazole;
5-[1-(2-Chloro-6-methyl-phenyl)-5-methyl-1H-imidazol-4-yl]-3-(4-methoxy-phenyl)-[1,2,4]oxadiazole;
5-[1-(2-Chloro-phenyl)-2,5-dimethyl-1H-imidazol-4-yl]-3-(2,4-dimethoxy-phenyl)-[1,2,4]oxadiazole;
5-(1-(2-Chlorophenyl)-2,5-dimethyl-1H-imidazol-4-yl)-3-(2,5-dimethoxyphenyl)-1,2,4-oxadiazole;
5-[1-(2-Chloro-phenyl)-2,5-dimethyl-1H-imidazol-4-yl]-3-(3,4,5-trimethoxy-phenyl)-[1,2,4]oxadiazole;
4-{5-[1-(2-Chloro-phenyl)-2,5-dimethyl-1H-imidazol-4-yl]-[1,2,4]oxadiazol-3-yl}-3-methoxy-benzoic acid methyl ester;
5-[1-(2-Chloro-phenyl)-2,5-dimethyl-1H-imidazol-4-yl]-3-(2-fluoro-4-methoxy-phenyl)-[1,2,4]oxadiazole;
4-{5-[1-(2-Chloro-phenyl)-2,5-dimethyl-1H-imidazol-4-yl]-[1,2,4]oxadiazol-3-yl}-2-methyl-benzoic acid methyl ester;
5-[1-(2-Chloro-phenyl)-2,5-dimethyl-1H-imidazol-4-yl]-3-(3-methoxy-phenyl)-[1,2,4]oxadiazole;
5-[1-(2-Methoxy-phenyl)-2,5-dimethyl-1H-imidazol-4-yl]-3-(3,4,5-trimethoxy-phenyl)-[1,2,4]oxadiazole;
5-[2-Bromo-1-(2-chloro-phenyl)-5-methyl-1H-imidazol-4-yl]-3-(3,4,5-trimethoxy-phenyl)-[1,2,4]oxadiazole;
5-[5-(2-Chlorophenyl)-1-methyl-imidazol-2-yl]-3-(3,4,5-trimethoxyphenyl)-1,2,4-oxadiazole;
5-[2-(2-Chlorophenyl)-3-methyl-imidazol-4-yl]-3-(3,4,5-trimethoxyphenyl)-1,2,4-oxadiazole;
4-[5-[1-(2-Chloro-6-methyl-phenyl)-5-methyl-imidazol-4-yl]-1,2,4-oxadiazol-3-yl]-3-methoxy-benzoic acid;
4-{5-[1-(2-Chloro-phenyl)-2,5-dimethyl-1H-imidazol-4-yl]-[1,2,4]oxadiazol-3-yl}-benzoic acid;
4-{5-[1-(2,6-Dimethyl-phenyl)-5-methyl-1H-imidazol-4-yl]-[1,2,4]oxadiazol-3-yl}-3-methoxy-benzoic acid;
4-{5-[1-(2,6-Dimethyl-phenyl)-5-methyl-1H-imidazol-4-yl]-[1,2,4]oxadiazol-3-yl}-2-methoxy-benzoic acid;
4-{5-[1-(2-Chloro-6-methyl-phenyl)-5-methyl-1H-imidazol-4-yl]-[1,2,4]oxadiazol-3-yl}-2-methoxy-benzoic acid;
(1-(2-Chlorophenyl)-5-methyl-4-(3-(3,4,5-trimethoxyphenyl)-1,2,4-oxadiazol-5-yl)-1H-imidazol-2-yl) methanol; and
1-(2-Chlorophenyl)-5-methyl-4-(3-(3,4,5-trimethoxyphenyl)-1,2,4-oxadiazol-5-yl)-1H-imidazole-2-carboxylic acid.

8. A pharmaceutical composition comprising a compound in accordance with claim 1 and a therapeutically inert carrier.

\* \* \* \* \*